US008655439B2

(12) United States Patent
Adachi et al.

(10) Patent No.: US 8,655,439 B2
(45) Date of Patent: Feb. 18, 2014

(54) SYSTEM AND METHOD OF SPEECH DISCRIMINABILITY ASSESSMENT, AND COMPUTER PROGRAM THEREOF

(75) Inventors: Shinobu Adachi, Osaka (JP); Koji Morikawa, Kyoto (JP)

(73) Assignee: Panasonic Corporation, Osaka (JP)

( * ) Notice: Subject to any disclaimer, the term of this patent is extended or adjusted under 35 U.S.C. 154(b) by 637 days.

(21) Appl. No.: 12/959,513

(22) Filed: Dec. 3, 2010

(65) Prior Publication Data

US 2011/0071828 A1 Mar. 24, 2011

Related U.S. Application Data

(63) Continuation of application No. PCT/JP2009/007111, filed on Dec. 22, 2009.

(30) Foreign Application Priority Data

Dec. 22, 2008 (JP) ................................ 2008-326176

(51) Int. Cl.
*A61B 5/04* (2006.01)

(52) U.S. Cl.
USPC .......................................... 600/544; 704/200

(58) Field of Classification Search
USPC ........ 600/544, 545; 607/57; 381/60; 704/200
See application file for complete search history.

(56) References Cited

U.S. PATENT DOCUMENTS

| | | | | |
|---|---|---|---|---|
| 5,601,091 | A | 2/1997 | Dolphin | |
| 6,602,202 | B2 * | 8/2003 | John et al. | 600/559 |
| 2006/0101079 | A1 | 5/2006 | Morikawa et al. | |
| 2006/0114222 | A1 | 6/2006 | Araki et al. | |
| 2009/0259277 | A1 * | 10/2009 | Cornejo Cruz et al. | 607/57 |

FOREIGN PATENT DOCUMENTS

| | | |
|---|---|---|
| JP | 63-255041 | 10/1988 |
| JP | 06-114038 | 4/1994 |
| JP | 07-039540 | 2/1995 |
| JP | 09-038069 | 2/1997 |
| JP | 2006-023566 | 1/2006 |
| WO | 2006/003901 A1 | 1/2006 |

OTHER PUBLICATIONS

Co-pending U.S. Appl. No. 13/037,479, filed Mar. 1, 2011 (application provided).

(Continued)

*Primary Examiner* — Navin Natnithithadha
*Assistant Examiner* — Etsub Berhanu
(74) *Attorney, Agent, or Firm* — Renner, Otto, Boisselle & Sklar, LLP

(57) ABSTRACT

A speech discriminability assessment system includes: a biological signal measurement section for measuring an electroencephalogram signal of a user; a presented-speech sound control section for determining a speech sound to be presented to the user by referring to a speech sound database retaining a plurality of monosyllabic sound data; an audio presentation section for presenting an audio associated with the determined speech sound to the user; a character presentation section for presenting a character associated with the determined speech sound to the user, subsequent to the presentation of the audio by the audio presentation section; an unexpectedness detection section for detecting presence or absence of an unexpectedness signal from the measured electroencephalogram signal of the user, the unexpectedness signal representing a positive component at 600 ms±100 ms after a time point when the character was presented to the user; and a speech sound discriminability determination section for determining a speech sound discriminability based on a result of detection by the unexpectedness detection section.

18 Claims, 13 Drawing Sheets

(56) References Cited

OTHER PUBLICATIONS

Adachi et al., "Event-related potentials elicited by unexpected visual stimuli after voluntary actions", International Journal of Psychophysiology, 2007, pp. 238-243.
Kazuoki Kodera, Shindan to Chiryosha, "Hochoki Fittingu No Kangaekata" (or "Concept of Hearing Aid Fitting"), 1999, p. 172 and an English translation.
Kaga et al., "Event-Related Potential (ERP) Manual-mailing concerning P300", Shinohara Shuppan Shinsha, 1995 and partial English translation.
Duncan-Johnson et al., "On Quantifying Surprise: The Variation of Event-Related Potentials with Subjective Probability", Psychophysiology vol. 14, No. 5, 1997, pp. 456-467.
Kanzaki et al., "Hochoki Q&A—Yoriyoi Fittingu Notameni", (or "Hearing aids Q&A—For better Fitting"), Kanehara & Co., Ltd., 2001, p. 79 and an English translation.
"Shin Seirishinrigaku" (or "New Physiopsychology"), supervised by Hiroshi Miyata, vol. 2, pp. 14-15 and a partial English translation, ISBN4-7628-2094-6.

* cited by examiner

*FIG.3A*

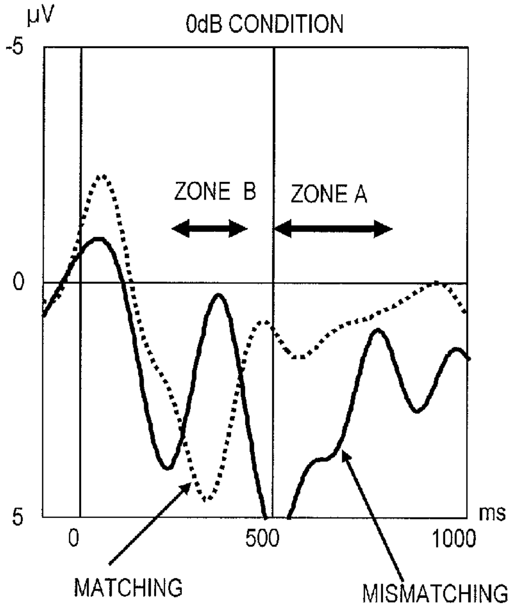

*FIG.3B*

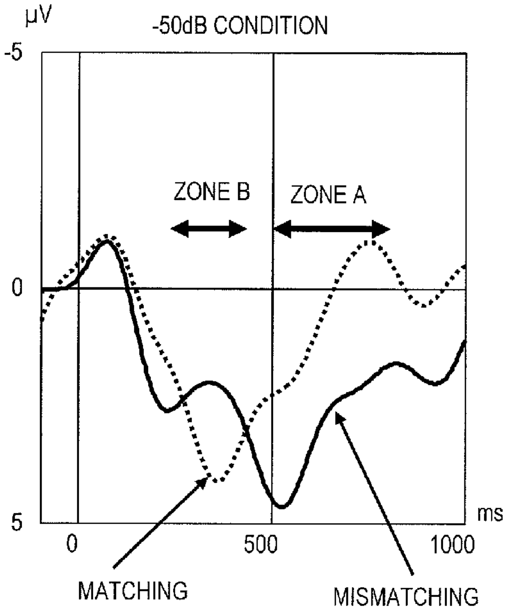

*FIG.4*

<table>
<tr><td colspan="2" rowspan="3"></td><td colspan="3">UNEXPECTEDNESS SIGNAL</td></tr>
<tr><td rowspan="2">YES</td><td colspan="2">NO</td></tr>
<tr><td>THERE IS P300</td><td>NO P300</td></tr>
<tr><td rowspan="2">AUDIO AND CHAR-ACTER</td><td>MATCH-ING</td><td>(A) HEARD TO BE A WRONG SPEECH SOUND</td><td>(B) CORRECTLY HEARD</td><td>(B') CHARACTER STIMULATION WAS NOT BEING WATCHED</td></tr>
<tr><td>UN-MATCH-ING</td><td>(C) POSSIBILY CORRECTLY HEARD</td><td>(D) HEARD WRONG TO BE THE SPEECH SOUND OF THIS CHARACTER</td><td>(D') CHARACTER STIMULATION WAS NOT BEING WATCHED</td></tr>
</table>

*FIG. 8*

71

| AUDIO FILE | CHAR-ACTER | GROUP | | |
|---|---|---|---|---|
| | | ROUGH CATEGORY | MEDIUM CATEGORY | FINE CATEGORY |
| a.wav | あ | 0 | 0 | 0 |
| i.wav | い | 0 | 0 | 0 |
| u.wav | う | 0 | 0 | 0 |
| e.wav | え | 0 | 0 | 0 |
| o.wav | お | 0 | 0 | 0 |
| ka.wav | か | 1 | 2 | 0 |
| sa.wav | さ | 1 | 1 | 0 |
| ta.wav | た | 1 | 2 | 0 |
| na.wav | な | 2 | 2 | 1 |
| ha.wav | は | 1 | 2 | 0 |
| ma.wav | ま | 2 | 2 | 1 |
| ya.wav | や | 2 | 1 | 0 |
| ra.wav | ら | 2 | 1 | 0 |
| wa.wav | わ | 2 | 1 | 0 |
| ga.wav | が | 2 | 2 | 2 |
| za.wav | ざ | 2 | 2 | 2 |
| da.wav | だ | 2 | 2 | 2 |
| ba.wav | ば | 2 | 2 | 2 |
| ... | ... | ... | ... | ... |

*FIG. 9*

| | | UNEXPECTEDNESS SIGNAL | | |
|---|---|---|---|---|
| | | YES | NO | |
| | | | THERE IS P300 | NO P300 |
| AUDIO AND CHAR-ACTER | MATCHING | × | ○ | — |
| | UNMATCH-ING | ○ | × | — |

*FIG.10*

| SPEECH SOUND | MATCHING | UNMATCHING | | |
|---|---|---|---|---|
| | | ROUGH CATEGORY | MEDIUM CATEGORY | FINE CATEGORY |
| あ (a) | ○ | ○ | ＼ | ＼ |
| い (i) | ○ | ○ | ＼ | ＼ |
| う (u) | ○ | ○ | ＼ | ＼ |
| え (e) | ○ | ○ | ＼ | ＼ |
| お (o) | ○ | ○ | ＼ | ＼ |
| か (ka) | ○ | ○ | ○ | ＼ |
| さ (sa) | ○ | ○ | ○ | ＼ |
| た (ta) | ○ | ○ | ○ | ＼ |
| な (na) | × | ○ | × | × |
| は (ha) | ○ | ○ | ○ | ＼ |
| ま (ma) | × | ○ | × | × |
| や (ya) | ○ | ○ | × | ＼ |
| ら (ra) | × | ○ | × | ＼ |
| わ (wa) | ○ | ○ | × | ＼ |
| が (ga) | × | ○ | × | × |
| ざ (za) | ○ | ○ | × | × |
| だ (da) | × | ○ | × | × |
| ば (ba) | ○ | ○ | × | × |
| ··· | ··· | ··· | ··· | ··· |

*FIG.13*

FITTING METHOD A

FITTING METHOD B

FITTING METHOD C

| SPEECH SOUND | MATCHING | | UNMATCHING | | | | | |
|---|---|---|---|---|---|---|---|---|
| | | | ROUGH CATEGORY | | MEDIUM CATEGORY | | FINE CATEGORY | |
| | CLARITY | AMPLITUDE | CLARITY | AMPLITUDE | CLARITY | AMPLITUDE | CLARITY | AMPLITUDE |
| あ (a) | ○ | 2.6 | ○ | 2.9 | - | | - | - |
| い (i) | ○ | 1.3 | ○ | 0.5 | - | | - | - |
| う (u) | ○ | 0.4 | ○ | 1.4 | - | | - | - |
| え (e) | ○ | 1.9 | ○ | 1.6 | - | | - | - |
| お (o) | ○ | 1.4 | ○ | 1.0 | - | | - | - |
| か (ka) | ○ | 0.7 | ○ | 0.0 | ○ | 2.2 | - | - |
| さ (sa) | ○ | 1.7 | ○ | 1.0 | ○ | 1.0 | - | - |
| た (ta) | ○ | 1.1 | ○ | 0.4 | ○ | 2.6 | - | - |
| な (na) | × | 9.0 | ○ | 3.0 | × | 4.6 | × | 12.4 |
| は (ha) | ○ | 0.4 | ○ | 1.3 | ○ | 2.7 | - | - |
| ま (ma) | × | 9.6 | ○ | 0.1 | × | 12.1 | × | 4.9 |
| や (ya) | ○ | 2.3 | ○ | 1.7 | × | 5.6 | - | - |
| ら (ra) | × | 3.6 | ○ | 1.6 | × | 1.8 | - | - |
| わ (wa) | ○ | 0.4 | ○ | 1.8 | × | 6.1 | - | - |
| が (ga) | × | 6.0 | ○ | 1.6 | × | 4.1 | × | 10.8 |
| ざ (za) | ○ | 0.4 | ○ | 1.1 | × | 3.0 | × | 2.7 |
| だ (da) | × | 15.0 | ○ | 0.5 | × | 2.0 | × | 9.8 |
| ば (ba) | ○ | 0.1 | ○ | 2.3 | × | 11.9 | × | 11.5 |
| ... | ... | | ... | | ... | | ... | ... |

*FIG.14*

| | LPP AMPLITUDE (UNMATCHING-MATCHING) | EVALUATION RESULT |
|---|---|---|
| FITTING METHOD A | 15.8μV | ◎ |
| FITTING METHOD B | 1.2μV | × |
| FITTING METHOD C | 6.5μV | △ |

*FIG.17A*

| WORD | EVALUATION |
|---|---|
| sit | ○ |
| meet | ○ |
| get | ○ |
| cat | ○ |
| come | ○ |
| hot | ○ |
| law | ○ |
| book | ○ |
| blue | △ |
| urge | ○ |
| star | △ |
| page | ○ |
| sky | △ |
| join | ○ |
| now | ○ |
| home | ○ |
| here | △ |
| care | ○ |
| ... | ... |

WORD-BY-WORD ASSESSMENT

*FIG.17B*

| PHONETIC SYMBOL | EVALUATION |
|---|---|
| i | ○ |
| e | ○ |
| æ | ○ |
| ə | △ |
| ʒ | ○ |
| ei | △ |
| ai | △ |
| au | △ |
| p | ○ |
| b | △ |
| t | ○ |
| d | △ |
| k | ○ |
| ... | ... |

PHONETIC SYMBOL-BY-PHONETIC SYMBOL ASSESSMENT

SYSTEM AND METHOD OF SPEECH DISCRIMINABILITY ASSESSMENT, AND COMPUTER PROGRAM THEREOF

This is a continuation of International Application No. PCT/JP2009/007111, with an international filing date of Dec. 22, 2009, which claims priority of Japanese Patent Application No. 2008-326176, filed on Dec. 22, 2008, the contents of which are hereby incorporated by reference.

BACKGROUND OF THE INVENTION

1. Field of the Invention

The present invention relates to a technique of assessing whether a speech sound has actually been aurally comprehended or not. More specifically, the present invention relates to a speech discriminability assessment system for making an assessment of speech sound discriminability, which is needed for assessing the degree of "fitting" of a hearing aid or the like to provide a sound of appropriate loudness for each individual user by adjusting the amount of sound amplification. "Discriminability" is sometimes referred to as "discrimination score".

2. Description of the Related Art

In recent years, for reasons such as the aging society, increased opportunities for listening to loud music for long hours, and so on, more and more people are suffering from presbycusis or hypacusia associated with acoustic traumas, and there is an increasing number of users who use hearing aids in order to aurally comprehend conversations in daily life more clearly.

Although the basic function of a hearing aid is sound amplification, the amount of sound amplification must be adjusted with respect to each user. For example, if the amount of amplification is insufficient, a sound pressure above the hearing threshold level will not be obtained, thus causing a problem in that the user cannot hear sounds. On the other hand, if more than a necessary amplification is applied, the UCL (uncomfortable level: a sound which is so loud that the user may feel uncomfortable) may be exceeded, in which case the user will feel uncomfortable. Therefore, before beginning use of a hearing aid, "fitting" is required for adjusting the amount of amplification so as to attain a sound of an appropriate loudness, which is neither too loud nor too soft, with respect to each user.

Fitting is generally performed based on each user's audiogram. An "audiogram" is a result of evaluating how a pure tone is "heard": for example, a diagram in which, for each of a number of sounds of different frequencies, the smallest sound pressure level (decibel value) that the user can hear is plotted against frequency. Currently, however, a number of fitting methods are diversely present, and there is no one established fitting method that can determine an optimum amount of sound amplification with respect to any and every user for improving the conversational listening comprehension discriminability from his or her audiogram alone. Possible reasons are that an audiogram is not in one-to-one correspondence with a conversational listening comprehension ability, and that a person suffering from hypacusia has a narrow range of sound pressure that is felt to him or her as an appropriate loudness, for example.

Therefore, in order to evaluate the degree of fitting, a speech discriminability assessment for assessing whether a speech sound has actually been aurally comprehended or not is needed, and even after beginning use of a hearing aid, re-fitting must be performed by utilizing results of speech discriminability assessment.

As used herein, a "speech discriminability assessment" is an assessment of listening comprehension ability for assessing whether a monosyllabic speech sound has been aurally comprehended or not. A monosyllabic speech sound means either a single vowel or a combination of a consonant and a vowel (e.g., "あ(a)"/"だ(da)"/"し(shi)"). Since the purpose of wearing a hearing aid is aural distinction in conversations, assessment results of speech sound discriminability are regarded as important.

Conventionally, speech discriminability assessment has been performed through the following procedure. First, by using the 57S list (50 monosyllables) or the 67S list (20 monosyllables) proposed by the Japan Audiological Society, a user is allowed to hear a monosyllabic audio. Next, the user is asked to answer what he or she has aurally comprehended of the presented speech sound through oral explanation, writing, or other methods. Then, an evaluator matches the answers against the list in order to calculate a correctness rate.

However, in the aforementioned assessment method, the user is required to make answers via oral explanation or writing, and the evaluator needs to determine the correctness of the user's answers through manual labor. Thus, this test has presented a large burden on the user and the evaluator.

Therefore, for example, Japanese Laid-Open Patent Publication No. 9-038069 (Hereinafter, Patent Document 1) discloses a speech discriminability assessment method which, in order to reduce the burden of the evaluator, employs a personal computer (PC) to automatically perform correctness determination. Specifically, Patent Document 1 proposes a method in which monosyllabic audios are presented to a user by using a PC; the user is asked to answer by using a mouse or via pen-touch technique; the answers are received as inputs to the PC; and correctness determinations as to the presented audios and answer inputs are automatically made. Since answer inputs are received by using a mouse or via pen-touch technique, there is no need for the evaluator to analyze and distinguish the user's answers (which are given by oral explanation or writing), whereby the trouble of the evaluator is greatly reduced.

Moreover, for example, Japanese Laid-Open Patent Publication No. 6-114038 (Hereinafter, Patent Document 2) discloses a speech discriminability assessment method in which, after audio presentation, possible choices of speech sounds are presented in the form of text characters, thus reducing the user's burden of making answer inputs. In Patent Document 2, choices are limited to only a small number so that the relevant speech sound can be found among the small number of characters, whereby the user's trouble of finding the character is reduced. Also in Patent Document 2, a PC is used to receive answer inputs, thus reducing the evaluator's burden.

However, in the speech discriminability assessment methods described in Patent Document 1 and Patent Document 2, the user still needs to make answer inputs. Such an answer-inputting operation still exists and presents a burden on the user. In particular, it is presumably not easy for people suffering from hypacusia or elderly people who are unaccustomed to working on a PC to make answer inputs by using a mouse or a touch pen. There has also been a possibility that the wrong monosyllable matrix may be inadvertently selected through a manipulation mistake, in which case the speech sound discriminability may not be correctly evaluated.

SUMMARY OF THE INVENTION

An objective of the present invention is to realize a speech discriminability assessment system in which the user does not need to perform cumbersome answer-inputting.

A speech discriminability assessment system according to the present invention comprises: a biological signal measurement section for measuring an electroencephalogram signal of a user; a presented-speech sound control section for determining a speech sound to be presented to the user by referring to a speech sound database retaining a plurality of monosyllabic sound data; an audio presentation section for presenting an audio associated with the determined speech sound to the user; a character presentation section for presenting a character associated with the determined speech sound to the user, subsequent to the presentation of the audio by the audio presentation section; an unexpectedness detection section for detecting presence or absence of an unexpectedness signal from the measured electroencephalogram signal of the user, the unexpectedness signal representing a positive component at 600 ms±100 ms after a time point when the character was presented to the user; and a speech sound discriminability determination section for determining a speech sound discriminability based on a result of detection by the unexpectedness detection section.

The presented-speech sound control section may present a character that does not match the audio with a predetermined frequency of occurrence.

The speech sound discriminability determination section may be operable to: when the character presented to the usermatches the audio presented to the user, make a low discriminability determination if a positive component exists at 600 ms±100 ms based on a point of presenting the character as a starting point, and make a high discriminability determination if no positive component exists at 600 ms±100 ms based on a point of presenting the character as a starting point; and when the character presented to the user does not match the audio presented to the user, make a high discriminability determination if a positive component exists at 600 ms±100 ms based on a point of presenting the character as a starting point, and make a low discriminability determination if no positive component exists at 600 ms±100 ms based on a point of presenting the character as a starting point.

The speech discriminability assessment system may further comprise a P300 component detection section for, from the electroencephalogram signal of the user as measured by the biological signal measurement section, determining presence or absence of a positive component at 300 ms±50 ms based on a point of presenting the character as a starting point, wherein, if the unexpectedness detection section determines that no positive component exists, the P300 component detection section may determine presence or absence of a positive component at 300 ms±50 ms, and the speech sound discriminability determination section may determine the speech sound discriminability based on a result of detection by the unexpectedness detection section and on a result of detection by the P300 component detection section.

The speech sound discriminability determination section may be operable to: when the character presented to the user matches the audio presented to the user, make a low discriminability determination if a positive component exists at 600 ms±100 ms based on a point of presenting the character as a starting point; make a high discriminability determination if no positive component exists at 600 ms±100 ms based on a point of presenting the character as a starting point and a positive component exists at 300 ms±100 ms based on a point of presenting the character as a starting point; and determine a failure of the user to look at the character presented at the character presentation section if no positive component exists at 600 ms±100 ms based on a point of presenting the character as a starting point and no positive component exists at 300 ms±100 ms based on a point of presenting the character as a starting point; and when the character presented to the user does not match the audio presented to the user, make a high discriminability determination if a positive component exists at 600 ms±100 ms based on a point of presenting the character as a starting point; make a low discriminability determination if no positive component exists at 600 ms±100 ms based on a point of presenting the character as a starting point and a positive component exists at 300 ms±100 ms based on a point of presenting the character as a starting point; and determine a failure of the user to look at the character presented at the character presentation section if no positive component exists at 600 ms±100 ms based on a point of presenting the character as a starting point and no positive component exists at 300 ms±100 ms based on a point of presenting the character as a starting point.

In the speech sound database, an audio, a character, and a group concerning likelihood of confusion may be associated with a common speech sound.

In the speech sound database, an audio, a character, and a group concerning likelihood of confusion may be associated with each of a plurality of speech sounds.

Referring to the groups concerning likelihood of confusion in the speech sound database, the presented-speech sound control section may present a character not associated with the audio with a predetermined frequency of occurrence.

The speech sound discriminability determination section may evaluate a speech sound discriminability with respect to each group concerning likelihood of confusion when the audio and the character are of different speech sounds, in addition to when the character presented to the user matches the audio presented to the user.

The speech discriminability assessment system may further comprise a speech sound conversion control section for converting an audio stored in the speech sound database into a plurality of kinds of audios in accordance with different fitting methods for a hearing aid worn by the user.

When the plurality of kinds of audios converted by the speech sound conversion control section are presented via the audio presentation section, the speech sound discriminability determination section may make a comparison between amplitudes of the event-related potentials obtained for the different fitting methods, and determine a fitting method that is suitable to the user in accordance with a result of comparison.

With respect to either matching or mismatching between the audio and the character, the unexpectedness detection section may store information of amplitude of an event-related potential at 600 ms±100 ms based on a point of presenting the character as a starting point, and determine a change in the amplitude of the event-related potential with respect to either matching or mismatching between the audio and the character; and the presented-speech sound control section may be operable to: if the change in amplitude of the event-related potential when the audio and the character are matching is equal to or less than the change in amplitude of the event-related potential when the audio and the character are mismatching, increase a frequency of selecting a character that matches the presented audio; and if the change in amplitude of the event-related potential when the audio and the character are matching is greater than the change in amplitude of the event-related potential when the audio and the character are mismatching, increase a frequency of selecting a character that does not match the presented audio.

An speech discriminability assessment method according to the present invention comprises the steps of: determining a speech sound to be presented by referring to a speech sound database retaining a plurality of monosyllabic sound data, and presenting the audio; determining a speech sound to be presented by referring to the speech sound database, and presenting the character subsequent to the presentation of the audio; measuring an electroencephalogram signal of a user; from the measured electroencephalogram signal of the user, determining presence or absence of a positive component at 600 ms±100 ms based on a point of presenting the character as a starting point; and determining a speech sound discriminability based on a result of detection by the unexpectedness detection section.

In the assessment method for speech sound discriminability, with a predetermined frequency of occurrence, the step of presenting the character presents a character that does not match the audio.

The step of determining presence or absence of a positive component may store information of amplitude of an event-related potential at 600 ms±100 ms based on a point of presenting the character as a starting point, with respect to either matching or mismatching between the audio and the character, and determine a change in the amplitude of the event-related potential with respect to either matching or mismatching between the audio and the character; and the step of presenting the character may comprise: if a change in amplitude of the event-related potential when the audio and the character are matching is equal to or less than a change in amplitude of the event-related potential when the audio and the character are mismatching, presenting the character with an increased frequency of selecting a character that matches the presented audio, and if a change in amplitude of the event-related potential when the audio and the character are matching is greater than a change in amplitude of the event-related potential when the audio and the character are mismatching, presenting the character with an increased frequency of selecting a character that does not match the presented audio.

A computer program, stored on a non-transitory computer-readable medium, for assessing speech sound discriminability according to the present invention, when executed by a computer, causes the computer to execute the steps of: determining a speech sound to be presented by referring to a speech sound database retaining a plurality of monosyllabic sound data, and presenting the audio; determining a speech sound to be presented by referring to the speech sound database, and presenting the character subsequent to the presentation of the audio; measuring an electroencephalogram signal of a user; from the measured electroencephalogram signal of the user, determining presence or absence of a positive component at 600 ms±100 ms based on a point of presenting the character as a starting point; and determining a speech sound discriminability based on a result of detection by the unexpectedness detection section.

The step of presenting the character to be executed by the computer may present a character that does not match the audio with a predetermined frequency of occurrence.

A speech discriminability assessment system according to the present invention comprises: a presented-speech sound control section for determining a speech sound to be presented to a user by referring to a speech sound database retaining a plurality of monosyllabic sound data, and performing control so that an audio associated with the determined speech sound is presented to the user via an audio presentation section for presenting an audio and subsequently a character associated with the determined speech sound is presented to the user via a character presentation section for presenting a character; an unexpectedness detection section for detecting presence or absence of an unexpectedness signal from an electroencephalogram signal of the user measured by a biological signal measurement section for measuring an electroencephalogram signal of the user, the unexpectedness signal representing a positive component at 600 ms±100 ms based on a point of presenting the character to the user as a starting point; and a speech sound discriminability determination section for determining a speech sound discriminability based on a result of detection by the unexpectedness detection section.

According to the present invention, based on matching/mismatching between a presented audio and a presented character and on the presence or absence of and the amplitude an unexpectedness signal obtained from an electroencephalogram of a user, aural distinction as to speech sounds can be evaluated quantitatively and automatically. Thus, a speech discriminability assessment is realized which does not require the user to make cumbersome answer inputting, thus reducing the burden on both an evaluator and the user.

Other features, elements, processes, steps, characteristics and advantages of the present invention will become more apparent from the following detailed description of preferred embodiments of the present invention with reference to the attached drawings.

BRIEF DESCRIPTION OF THE DRAWINGS

FIGS. 3A and 3B are waveform diagrams each obtained by taking a total arithmetic mean of an event-related potential from −100 ms to 1000 ms based on a point of presenting a character stimulation as 0 ms, with respect to mismatching/matching button pressing.

FIG. 4 is a diagram showing exemplary case differentiations for an assessment method for aural distinction as to speech sounds, based on matching/mismatching between a presented audio and a presented character and on the presence or absence of an unexpectedness signal/P300 in an event-related potential after a character stimulation is presented.

FIG. 8 is a diagram showing an example of a speech sound DB 71.

FIG. 9 is a diagram showing exemplary assessment criteria for discriminability.

FIG. 10 is a diagram showing exemplary results of speech discriminability assessment.

FIG. 13 is a diagram showing amplitudes of various event-related potentials respectively calculated for fitting methods A to C.

FIG. 14 is a diagram showing exemplary assessment results of fitting methods.

FIGS. 17A and 17B are diagrams describing evaluations in languages other than Japanese.

DETAILED DESCRIPTION OF PREFERRED EMBODIMENTS

Figure 1:
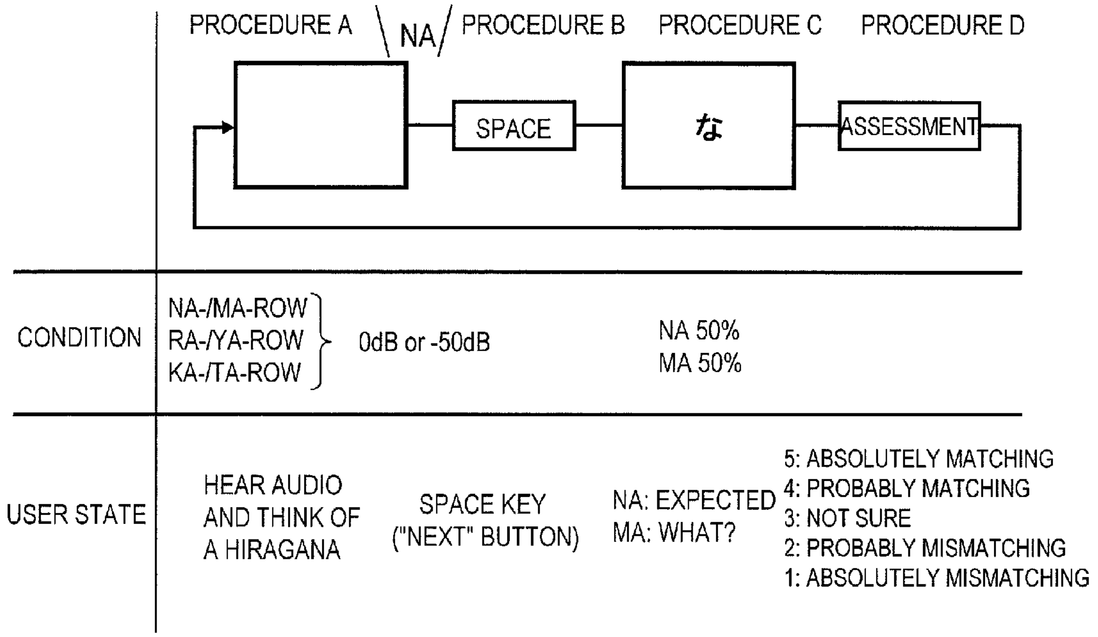
FIG. 1 is a diagram describing an experimental procedure in outline.

Hereinafter, with reference to the attached drawings, embodiments of the speech discriminability assessment system according to the present invention will be described.

A speech discriminability assessment system according to the present invention is used for assessing a speech sound discriminability by utilizing an electroencephalogram. More specifically, the speech discriminability assessment system is used for sequentially presenting a monosyllabic speech sound (s) in the form of an audio and a character to a user, allowing the user to confirm whether the audio and the character matched or not, and assessing aural distinction as to speech sounds, where an event-related potential based on the point of character presentation as a starting point is utilized as an index. In the present specification, to "present an audio" means to output an auditory stimulation, e.g., outputting an audio through a loudspeaker. On the other hand, to "present a character" means to output a visual stimulation, e.g., displaying a character on a screen of a TV or the like.

The inventors have performed an experiment where, on the premise that a monosyllabic speech sound(s) is sequentially presented in the form of an audio and a character (hiragana), an event-related potential of a user who confirms whether the audio and the character are identical is measured based on the point of character presentation as a starting point, under a condition such that characters which do not match the audio are presented with a predetermined probability. It was thus found that, in an event-related potential based on the point of character stimulation as a starting point, an unexpectedness signal (a positive component near about 600 ms) is induced when a character not matching a hiragana that was evoked from the audio is presented, and that a P3 component is induced when a matching character is presented. Based on this finding, the inventors have realized that aural distinction as to audios can be evaluated based on matching/mismatching between the presented audio and character, and on the presence or absence of an unexpectedness signal in the event-related potential based on the point of character presentation as a starting point.

These will be described in more detail below. Firstly, a speech discriminability assessment paradigm which the inventors have conceived of in order to realize a speech discriminability assessment which does not require answer inputs by a user, and an electroencephalogram measurement experiment which was conducted by the inventors, will be described. Thereafter, as an embodiment, an outline of a speech discriminability assessment apparatus for assessing whether a speech sound has been aurally comprehended or not and a construction and operation of a speech discriminability assessment system including the speech discriminability assessment apparatus will be described.

1. Speech Discriminability Assessment Paradigm

The inventors have hitherto found that a characteristic component appears in an event-related potential in connection with mismatching between an anticipation and an actual result, i.e., a positive component near about 600 ms based on the point of obtaining an mismatching result as a starting point (hereinafter referred to as an "unexpectedness signal") (literature for reference: Adachi et al., International Journal of Psychophysiology, 2007).

When speech sounds cannot be aurally comprehended, the user is in a situation where he or she cannot anticipate the correct character even if they hear an audio. With this in mind the inventors have realized that, if this situation can be detected by using an unexpectedness signal, a speech discriminability assessment can be performed without answer inputs being made by the user.

Furthermore, the inventors have conceived of an assessment paradigm where characters which do no match a given audio are sporadically presented with a predetermined frequency of occurrence (e.g., once in twice). In an experiment where an audio is simply presented twice, an unexpectedness concerning the degree of matching as to the speech sound can be detected, but there is a possibility that both audios may be heard wrong, thus making it impossible to evaluate whether listening comprehension as to speech sounds has been achieved or not.

Accordingly, characters which do not match the audio are sporadically presented with a predetermined frequency of occurrence (e.g., once in twice), thus making it possible to determine matching/mismatching between at least the previously heard audio and each character, since a character will not be mistaken for another hiragana by eyesight. In addition, since mismatching characters are sporadically presented with a predetermined frequency of occurrence, every trial requires a determination (as to mismatching/matching) of the stimulation, whereby the user's attention to the character is automatically increased, and sustainment of attention is facilitated. As a result, it becomes possible to measure a clearer signal component because a decrease in the amplitude of the electroencephalogram signal due to a decreased attention to a stimulation is reduced. Moreover, under a condition that a character matching the audio will always be presented, there is a possibility of not making a correct assessment of listening comprehension, because "mismatching" will be absent both in the case where an audio stimulation was correctly aurally comprehended and in the case where only acknowledgement of a character stimulation was made without comparing the audio stimulation and the character stimulation. On the other hand, by allowing mismatching stimulations to be sporadically presented, it becomes possible to separate the above two states.

As from the above, the assessment paradigm proposed by the inventors, where mismatching character stimulations are presented with a predetermined probability on the premise that a character will be presented after presenting an audio, is the first to realize a speech discriminability assessment without answer inputs, where it is only necessary to think of a hiragana corresponding to an audio and confirm a subsequently-presented character.

In an assessment where mismatching character stimulations are presented with a predetermined probability on the premise that a character stimulation will be presented after presenting an audio stimulation, a user only needs to think of a hiragana corresponding to the audio and confirm a subsequently-presented character, whereby a speech discriminability assessment which does not require answer inputs by the user can be realized.

2. Description of Experiment

Hereinafter, with reference to FIG. 1 to FIG. 3B, the experiment and experimental results will be described.

Five undergraduate or graduate students with normal hearing participated in the experiment. The electroencephalogram was measured from the Pz (International 10-20 system) on the scalp, relative to the right earlobe, with a sampling frequency of 200 Hz and a time constant of 1 second. It was subjected to a 1 to 6 Hz digital band-pass filter off-line. Each character was presented on a 21-inch LCD, which was placed 1 m in front of the participant, with a viewing angle of 3°×3°.

FIG. 1 shows the experimental procedure in outline.

First, a monosyllabic audio was presented in procedure A. With reference to "HOCHOKI FITTINGU NO KANGAEKATA (or "Concept of Hearing Aid Fitting") (Kazuoki KODERA, Shindan To Chiryosha, 1999), the stimulation speech sound was selected from among a pair of na- and ma-rows, a pair of ra- and ya-rows, and a pair of ka- and ta-rows, which are known to mutually induce mistakes in listening comprehension. Each experimental participant was instructed to think of a hiragana upon hearing the audio.

Figure 16:
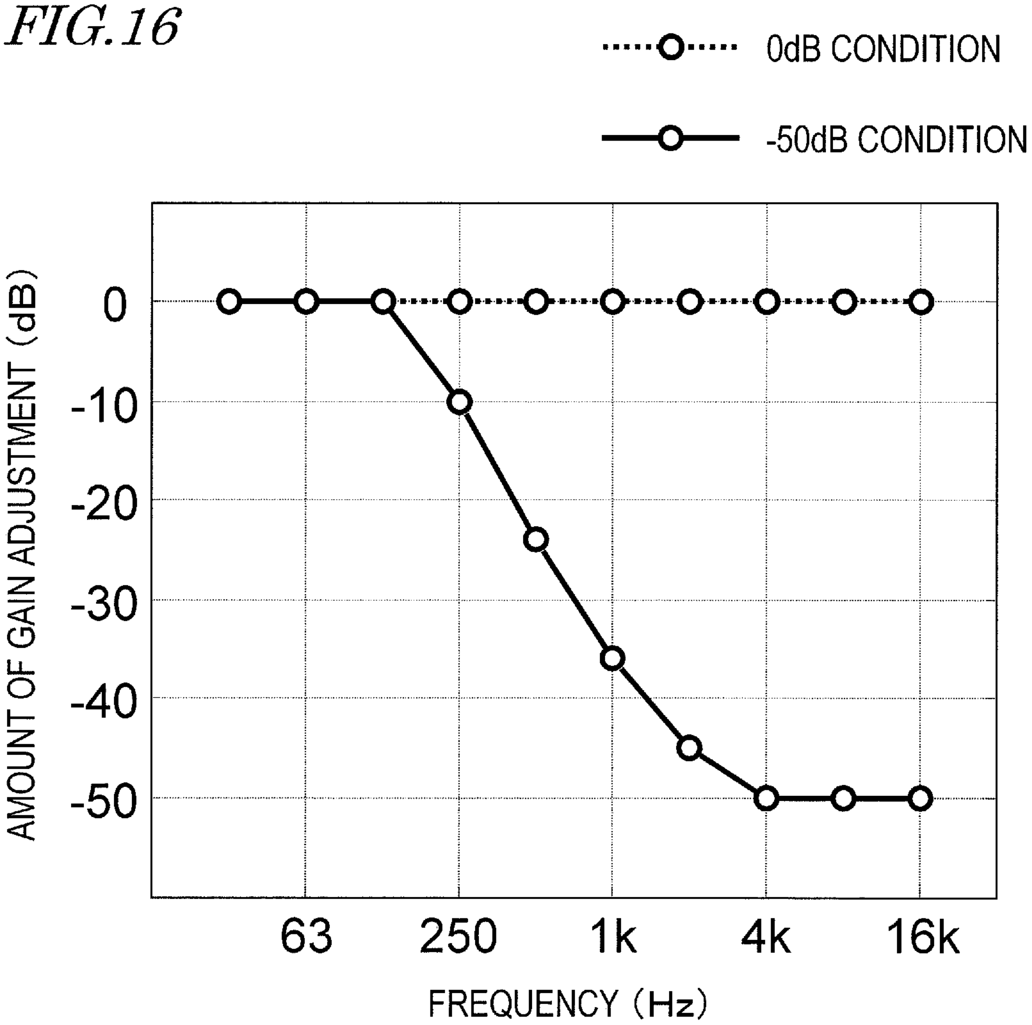
FIG. 16 is a diagram showing amounts of gain adjustment for different frequencies.

In order to examine a relationship between ease of aural distinction of audios and the amplitude of the unexpectedness signal, each presentation was performed in either of the two conditions: a condition of not altering the frequency gain (0 dB condition: easy to aurally distinguish) and a condition of gradually adjusting (attenuating) the gains for frequencies from 250 Hz to 16 kHz to −50 dB (−50 dB condition: difficult to aurally distinguish). FIG. 16 shows amounts of gain adjustment for different frequencies.

Next, in procedure B, the experimental participant was asked to press the SPACE key on the keyboard. Procedure B, which concerns a button pressing for being able to proceed to procedure C, was introduced in this experiment to allow the participant to experience the character stimulation of procedure C at his or her own pace. This procedure is unnecessary in an actual assessment of speech sound discriminability because the unexpectedness signal will appear even if this button pressing is omitted.

In procedure C, a hiragana character was presented on a display. With a 50% probability, a hiragana not matching the audio presented in procedure A was presented. As each mismatching hiragana, a character in a different row from that of the audio was chosen, from within a pair of na- and ma-rows, a pair of ra- and ya-rows, or a pair of ka- and ta-rows (which are supposed to induce many mistakes in listening comprehension), while the vowel was not changed.

For example, if a hiragana "な(na)" was presented in procedure A, then "な" was to be presented under the matching condition, and "ま(ma)" was to be presented under the mismatching condition, in procedure C. If the participant aurally comprehended the audio correctly, he or she would feel expectedness in response to "な" being presented, and unexpectedness in response to "ま" being presented.

Procedure D involves a button pressing (numbers 1 to 5 on the keyboard) for confirming how mismatching the audio presented in procedure A and the character presented in procedure C were to the participant. The participant was supposed to press "5" to express "absolutely matching", "4" to express "probably matching", "3" to express "not sure", "2" to express "probably mismatching", and "1" to express "absolutely mismatching". Although the answering via a button pressing on the keyboard was introduced in this experiment to confirm whether unexpectedness was felt in response to a mismatching character being presented, and how difficult aural distinction was under the −50 dB condition, this procedure is unnecessary in an actual evaluate.

In the experiment conducted, procedure A to procedure D described above was repeated 72 times (72 trial).

Figure 2:
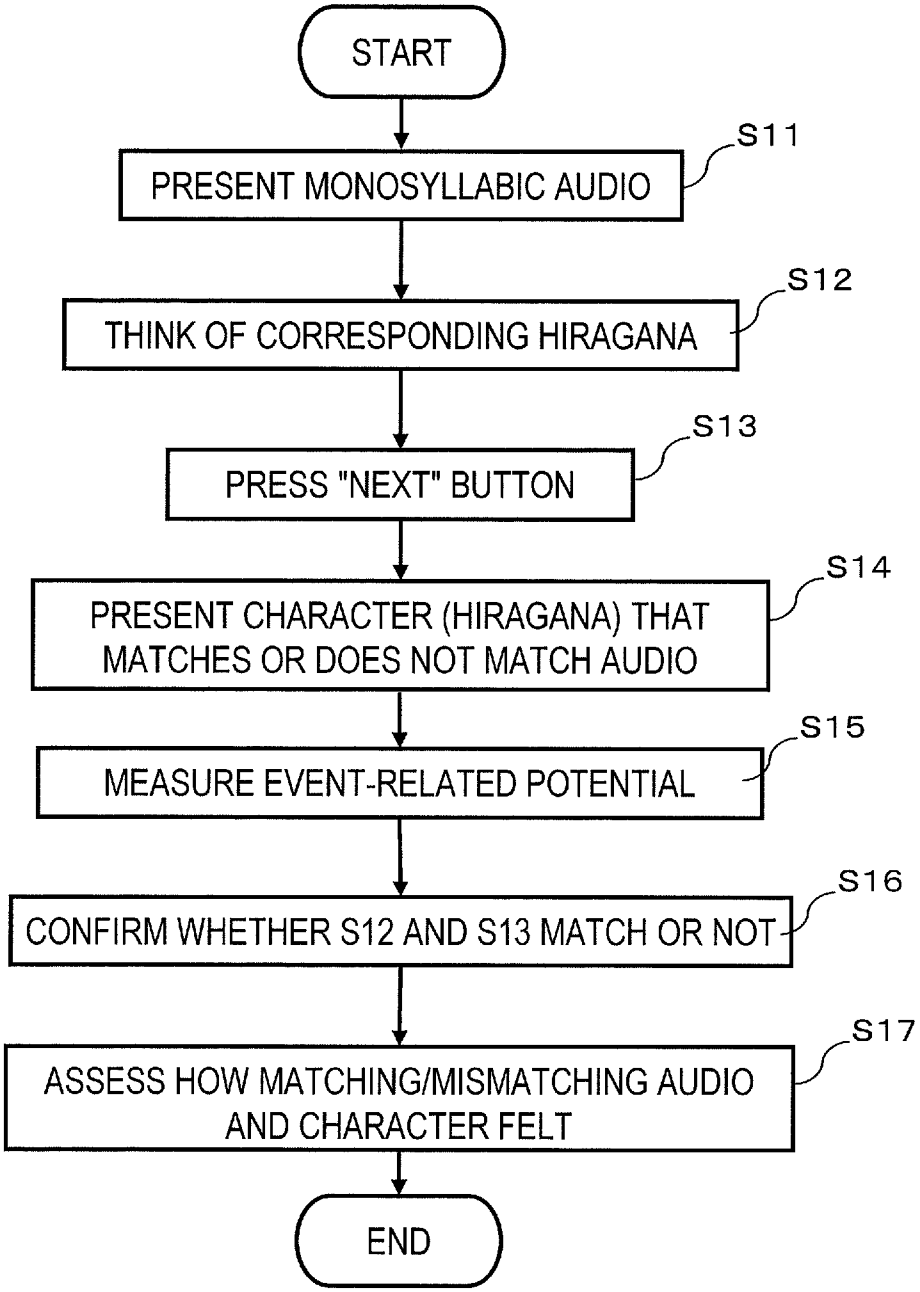
FIG. 2 is a flowchart showing a procedure corresponding to one trial.

FIG. 2 is a flowchart showing a procedure corresponding to one trial. In this flowchart, for ease of explanation, the operation of the apparatus and the operation of the experimental participant are both present.

Step S11 is a step of presenting a monosyllabic audio to the experimental participant. The audio was presented under the two conditions of the 0 dB condition and the −50 dB condition.

Step S12 is a step where the participant thinks of a corresponding hiragana upon hearing the monosyllabic audio.

Step S13 is a step where the participant presses the SPACE key as a "Next" button.

Step S14 is a step of presenting on a display a hiragana character matching the audio or a hiragana character mismatching the audio, both with a 50% probability as reckoned from step S13 as the starting point.

Step S15 is a step of measuring an event-related potential based on the point of presenting the character stimulation at step S14 as a starting point.

Step S16 is a step of confirming whether the hiragana which the participant thought of at step S12 matches the hiragana presented at step S14.

Step S17 is a step of answering how matching/mismatching they were felt to the participant at step S16, via number keys of 1 to 5.

The experimental results are described below.

First, results of button pressing assessment by the participant will be described. The rate of making an "absolutely matching" or "absolutely mismatching" assessment, meaning that the audio was clearly heard, was 36.6% under the −50 dB condition, which is significantly ($p<0.01$) smaller than that under the 0 dB condition of 87.5%. Moreover, incorrect assessments (making an "absolutely mismatching" or "probably mismatching" assessment for a matching stimulation, or making an "absolutely matching" or "probably matching" assessment for a mismatching stimulation) accounted for 14.6% under the −50 dB condition, which is significantly ($p<0.01$) greater than that under the 0 dB condition of 2.5%. These results indicate that listening comprehension of the audio was difficult for even a participant with normal hearing under the −50 dB condition.

FIGS. 3A and 3B show waveforms under the 0 dB condition and the −50 dB condition, each obtained by taking a total arithmetic mean of an event-related potential from −100 ms to 1000 ms based on a point of presenting a character stimulation as 0 ms, on the basis of matching/mismatching of stimulations and the participant's assessments. The arithmetic mean was taken with respect to "absolutely matching"/"probably matching" assessments for matching stimulations, and "absolutely mismatching"/"probably mismatching" assessments for mismatching stimulations. In FIGS. 3A and 3B, the horizontal axis represents time in units of ms, and the vertical axis represents potential in units of μV. As is clear from the scales shown in FIGS. 3A and 3B, the lower direction in each graph corresponds to plus (positive), and the upper direction corresponds to minus (negative). The baseline is set to an average potential from −100 to 0 ms.

In each of FIGS. 3A and 3B, the solid line represents an arithmetic mean waveform in the case where the participant felt "absolutely mismatching"/"probably mismatching", whereas the broken line represents an arithmetic mean waveform in the case where the participant felt "absolutely matching"/"probably matching" (i.e., the participant felt some matching). It can be confirmed from FIGS. 3A and 3B that, under both conditions of the 0 dB condition and the −50 dB condition, a late positive potential (LPP) appears in zone A (latency: 500 to 700 ms) in the case where the participant felt mismatching between the audio stimulation and the character stimulation, as compared to the case where some matching was felt. It is highly likely that this is an unexpectedness signal (a positive potential with a latency near about 600 ms) that reflects unexpectedness (a "What?" sentiment) concerning an mismatching character stimulation, which the inventors have discovered. Thus it can be said that, on the basis of the amplitude of an event-related potential with a latency from 500 to 700 ms since the timing of presenting the character stimulation, it is possible to detect whether the user has felt that the character stimulation is mismatching or not.

It can also be confirmed from FIGS. 3A and 3B that, in the case where the audio stimulation and the character stimulation are matching, a large positive component with a greater amplitude appears in zone B (latency 300 to 400 ms), as compared to the case where they are mismatching. This is considered as an electroencephalogram signal component called the P300 component, which reflects expectedness concerning a character stimulation ("a "That's it (=the character I expected)!" sentiment). According to "SHINSEIRISHINRIGAKU (or "New Physiopsychology") Vol. 2" (supervised by Yo MIYATA, Kitaoji Shobo, 1997), page 14, the "P300 component" is generally a positive component near a latency of 300 ms that is induced in response to a target stimulation in an oddball task.

Under the settings of this experiment, the P300 component also appeared with respect to a matching character stimulation; this is presumably because character stimulations not matching the audio stimulation were presented with a probability as high as 50%. Since the P300 component would not appear if the user were not looking at the character stimulation, the P300 component can be used as an index to determine whether the user has actually looked at and recognized the character stimulation (i.e., whether the character stimulation was not overlooked).

Moreover, the zone average potential of the positive component in zone A (500 to 700 ms) was 3.74 μV under the 0 dB condition, and 2.08 μV under the −50 dB condition, indicating that the value under the 0 dB condition was significantly greater ($p<0.05$). It is presumable that, under the −50 dB condition where listening comprehension of the audio is difficult, the degree of mismatching between the audio and the character reduces. Thus, it can be said that the amplitude of the unexpectedness signal reflects the degree of mismatching felt by the user.

The aforementioned unexpectedness signal and P300 component are identifiable by a method of applying threshold processing to peak amplitude levels near a latency of about 600 ms and near a latency of about 300 ms, or a method of creating a template from typical unexpectedness-signal and P300-component waveforms and calculating similarity levels with respect to such templates, for example. Note that such threshold values and templates may be those of a typical user as prestored, or generated for each individual person.

In this experiment, each arithmetic mean was taken from about 50 summations of the data of five participants, this being in order to confirm the fact that an unexpectedness signal is sure to appear in an event-related potential based on the point of character presentation as a starting point. However, identification of an unexpectedness signal is possible with no summations or only a small number of summations (e.g., several times), depending on the identification method.

In the present specification, in order to define a component of an event-related potential, a point in time after the lapse of a predetermined time since a given point is expressed as "about 300 ms", "near 600 ms", or the like. This means possible inclusion of a range around a specific point in time such as "300 ms" or "600 ms". Generally speaking, there are 30 to 50 ms of differences (shifts) in event-related potential waveform between individuals, according to table 1 on p. 30 of "JISHOUKANRENDENI (ERP) MANYUARU—P300 WO CHUSHINNI— (or "Event-Related Potential (ERP) Manual—mainly concerning P300—"), edited by Kimitaka KAGA et al., Shinohara Shuppan Shinsha, 1995)". Therefore, the terms "about X ms" and "near X ms" mean that a breadth of to 50 ms may exist before or after X ms (e.g., 300 ms±50 ms, 600 ms±50 ms).

Although the aforementioned "breadth of 30 to 50 ms" is a general example of an individual difference in the P300 component, greater individual differences exist between users with respect to the unexpectedness signal, which is later in latency than P300. Therefore, the unexpectedness signal is preferably treated as having a broader breadth, e.g., a breadth of about 100 ms.

Thus, it has been found through the experiment, under conditions where a monosyllabic speech sound(s) is sequentially presented in the forms of an audio and a character and the user is asked to confirm whether the audio and the character match, that: (1) an unexpectedness signal appears in an event-related potential based on the point of character stimulation as a starting point if the user feels that the audio and the character are mismatching; (2) in the aforementioned event-related potential, a P300 component appears if the user feels that the audio and the character are matching; and (3) the degree of mismatching between the audio and the character as felt by the user is reflected on the amplitude of the unexpectedness signal.

Hereinafter, with reference to FIG. 4, it will be demonstrated that assessment of speech sound discriminability is possible based on matching/mismatching between an audio and a character, and on the presence or absence of an unexpectedness signal/P300 component in an event-related potential based on the point of character presentation as a starting point.

FIG. 4 shows exemplary case differentiations for an assessment method for aural distinction as to speech sounds, based on matching/mismatching between a presented audio and a presented character and on the presence or absence of an unexpectedness signal/P300 in an event-related potential after a character stimulation is presented.

Cell (A) corresponds to a situation where an unexpectedness signal appeared although a character matching the audio was presented. This situation presumably means that the user heard the audio wrong and thought of a different hiragana, and therefore felt that the character stimulation was mismatching although the presented character really matched the audio. Therefore an assessment can be made that the audio was heard wrong.

Cell (B) corresponds to a situation where a character matching the audio was presented, and an unexpectedness signal did not appear, but a P300 component appeared. Since the user looked at the character and recognized that it matched the audio, an assessment can be made that the audio was correctly heard.

Cell (B') corresponds to a situation where neither an unexpectedness signal nor a P300 component appeared in response to a character matching the audio. In this case, an assessment can be made that the user was not looking at, or overlooked, the character stimulation.

Cell (C) corresponds to a situation where a character not matching the audio was presented and an unexpectedness signal appeared. Although there is a possibility that the user thought of a wrong hiragana which is identical to neither the presented character nor the audio (instead of the hiragana conforming to the presented audio), an assessment can be made that it is likely that a correct aural comprehension occurred.

Cell (D) corresponds to a situation where, although a character not matching the audio was presented, an unexpectedness signal did not appear but a P300 component appeared. Since the user felt that what was really an mismatching character was matching, an assessment can be made that the user wrongly heard the audio to be the speech sound represented by the character. In this case, it can be said that the presented combination of audio and character was likely to be confused by the user.

Cell (D') corresponds to a situation where neither an unexpectedness signal nor a P300 component appeared in response to a character not matching the audio. Similarly to Cell (B'), an assessment can be made that the user was not looking at, or overlooked, the character stimulation.

Cell (C) and Cell (D) are situations whose assessment is enabled by intentionally presenting a character not matching the audio. Since the assessment of Cell (D), which provides information as to how the viewing was conducted, is especially important, presentation of an mismatching character can be considered as effective. Moreover, isolation of Cell (B) from Cell (B'), and Cell (D) from Cell (D'), is enabled by using the presence or absence of a P300 component as an index, in addition to the presence or absence of an unexpectedness signal. In an actual scene of assessment, it is possible that the user may often fall asleep during the assessment and overlook the character stimulation. In addition, Cell (B) Cell (B') pertain to quite different assessments, as do Cell (D) and Cell (D'). Therefore, it is essential to separately evaluate these cells.

Now, effects of the experimental settings of sporadically presenting mismatching stimulations will be summarized. Firstly, the user's attention to character stimulations is automatically enhanced, and sustainment of attention is facilitated. This reduces a decrease in amplitude of the electroencephalogram signal associated with a decrease in attention to stimulations. Secondly, when mismatching character stimulations are presented with a high frequency of occurrence, a P300 component will be induced in response to matching character stimulations, thus making it possible to confirm that the user was actually carrying out the speech discriminability assessment task. What realizes the speech discriminability assessment shown in FIG. 4 is the use of the P300 component and the unexpectedness signal.

In the above description, it is illustrated that characters mismatching the audio are intentionally presented with a frequency of occurrence of once in twice. However this is only an example; it may be once in three times or once in four times, for example.

It is known that the amplitude of the P300 component changes in accordance with the rate of presenting stimulations (Duncan-Johnson and Donchin, 1977. "On Quantifying Surprise The Variation of Event-Related Potentials With Subjective Probability". Psychophysiology 14, 456-467). Therefore, in accordance with the rate of matching/mismatching, the threshold value for P300 component detection needs to be lowered when the rate of presenting matching character stimulations is high.

Thus, it has been found that listening comprehension of an audio can be evaluated based on the matching/mismatching between the audio and a character and on the presence or absence of an unexpectedness signal and a P300 component, without answer inputs being made by the user.

Based on the above exemplary case differentiations and assessment results thereof, the inventors have constructed speech discriminability assessment systems. Each speech discriminability assessment system described in the following Embodiments sequentially presents a monosyllabic speech sound(s) in the form of an audio and a character, and based on the matching/mismatching between the audio and the character and on the presence or absence of an unexpectedness signal and a P300 component in an event-related potential based on the point of character stimulation as a starting point, evaluates listening comprehension of speech sounds. Such a speech discriminability assessment system, which does not require answer inputs being made by the user, is unprecedentedly realized by the assessment paradigm conceived by the inventors.

3. Embodiment 1

Hereinafter, an embodiment of a speech discriminability assessment system utilizing an unexpectedness signal will be described.

First, a speech discriminability assessment system which sequentially presents an audio and a character, measures an event-related potential based on the point of character presentation as a starting point and detects an unexpectedness signal and/or a P300 component, and evaluates listening comprehension of speech sounds will be described in outline. Thereafter, the construction and operation of a speech discriminability assessment system including the speech discriminability assessment apparatus will be described.

3.1. Construction of Speech Discriminability Assessment System

Figure 5:
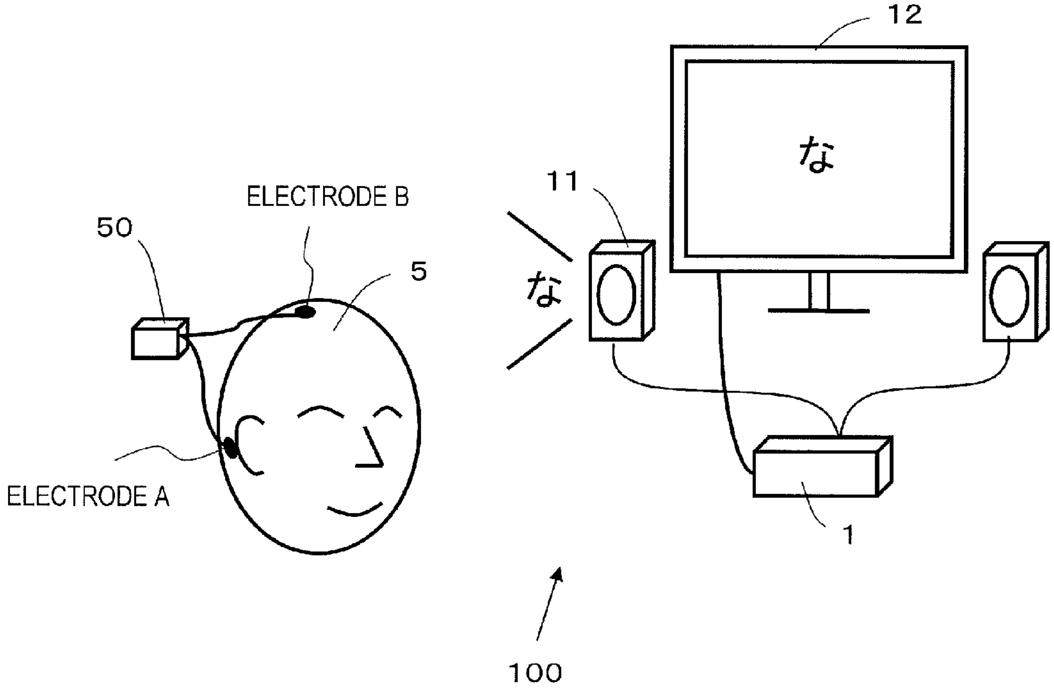
FIG. 5 is a diagram showing a construction and an environment of use for a speech discriminability assessment system 100 according to Embodiment 1.

FIG. 5 shows a construction and an environment of use for a speech discriminability assessment system 100 according to the present embodiment. The speech discriminability assessment system 100 is exemplified so as to correspond to a system construction of Embodiment 1 described later.

The speech discriminability assessment system 100 includes a speech discriminability assessment apparatus 1, an audio output section 11, a character output section 12, and a biological signal measurement section 50. The biological signal measurement section 50 includes at least two electrodes A and B. Electrode A is attached at a mastoid (under the root of an ear) of the user 5, whereas electrode B is attached at a position (so-called Pz) on the scalp of the user 5.

The speech discriminability assessment system 100 presents a monosyllabic speech sound(s) to the user 5 in the order of (1) an audio and (2) a character, and determines the presence or absence of an unexpectedness signal in an electroencephalogram (event-related potential) from the user 5 which is measured based on the point of character presentation as a starting point. In addition, if an unexpectedness signal did not appear, the speech discriminability assessment system 100 determines the presence or absence of a P300 component in the aforementioned event-related potential. Then, based on the matching/mismatching between the presented audio and the presented character and on the presence or absence of an unexpectedness signal and/or a P300 component, the speech discriminability assessment system 100 automatically realizes a speech discriminability assessment without answer inputs being made by the user 5.

An electroencephalogram from the user 5 is acquired by the biological signal measurement section 50 based on a potential difference between electrode A and electrode B. The biological signal measurement section 50 sends information corresponding to the potential difference to the speech discriminability assessment apparatus 1 in a wireless or wired manner. FIG. 5 illustrates an example where the biological signal measurement section 50 wirelessly sends this information to the speech discriminability assessment apparatus 1.

The speech discriminability assessment apparatus 1 performs sound pressure control of the audio used for speech discriminability assessment, controls presentation timing of the audio and the character, presents an audio via the audio output section 11 (e.g., loudspeakers) to the user 5, and presents a character via the character output section 12 (e.g., a display) to the user 5.

Although FIG. 5 illustrates the audio output section 11 as loudspeakers and the character output section 12 as a display, the audio output section 11 may be headphones, and the character output section 12 may be a head-mount display. By using headphones and a head-mount display, an enhanced mobility is provided, thus enabling a speech discriminability assessment in an actual environment of use of the user.

Figure 6:
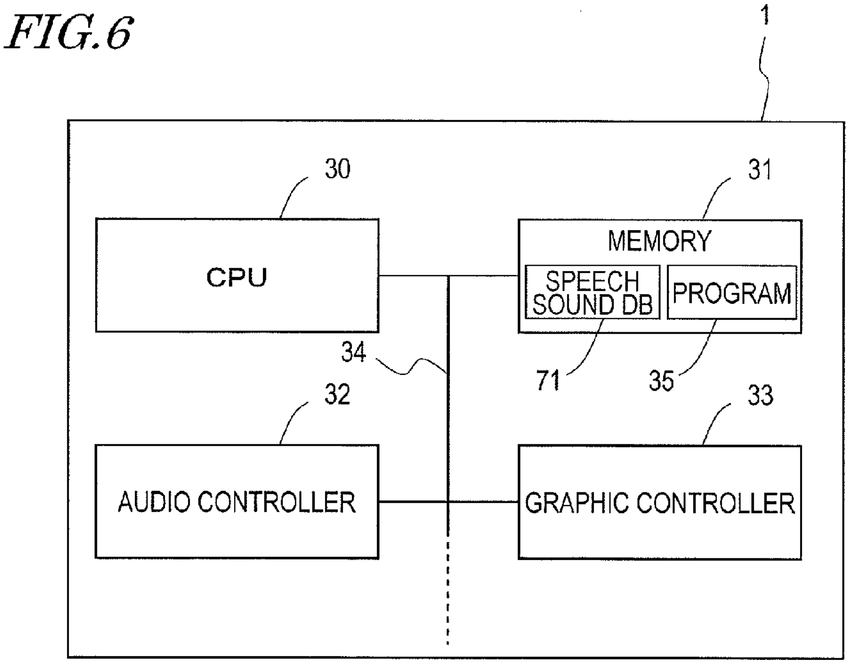
FIG. 6 is a diagram showing a hardware construction of the speech discriminability assessment apparatus 1.

FIG. 6 shows a hardware construction of the speech discriminability assessment apparatus 1 according to the present embodiment. The speech discriminability assessment apparatus 1 includes a CPU 30, a memory 31, an audio controller 32, and a graphic controller 33. These elements are interconnected via a bus 34 so that data exchange among them is possible.

The CPU 30 executes a computer program 35 which is stored in the memory 31. In accordance with the computer program 35, the speech discriminability assessment apparatus 1 performs a process of controlling the entire speech discriminability assessment system 100, by utilizing a speech sound DB 71 which is also stored in the same memory 31. This process will be described in detail later.

In accordance with instructions from the CPU 30, the audio controller 32 and the graphic controller 33 respectively generate an audio and a character to be presented, and output the generated audio signal and character signal to the audio output section 11 and the character output section 12.

Note that the speech discriminability assessment apparatus 1 may be implemented as a piece of hardware (e.g., a DSP) consisting of a semiconductor circuit having a computer program incorporated therein. Such a DSP can realize all functions of the aforementioned CPU 30, memory 31, audio controller 32, and graphic controller 33 on a single integrated circuit.

The aforementioned computer program 35 may be distributed on the market in the form of a product recorded on a storage medium such as a CD-ROM, or transmitted through telecommunication lines such as the Internet. Upon reading the computer program 35, a device having the hardware shown in FIG. 6 (e.g., a PC) is able to function as the speech discriminability assessment apparatus 1 according to the present embodiment. Note that the speech sound DB 71 does not need to be stored in the memory 31, but may be stored on a hard disk (not shown) which is connected to the bus 34.

Figure 7:
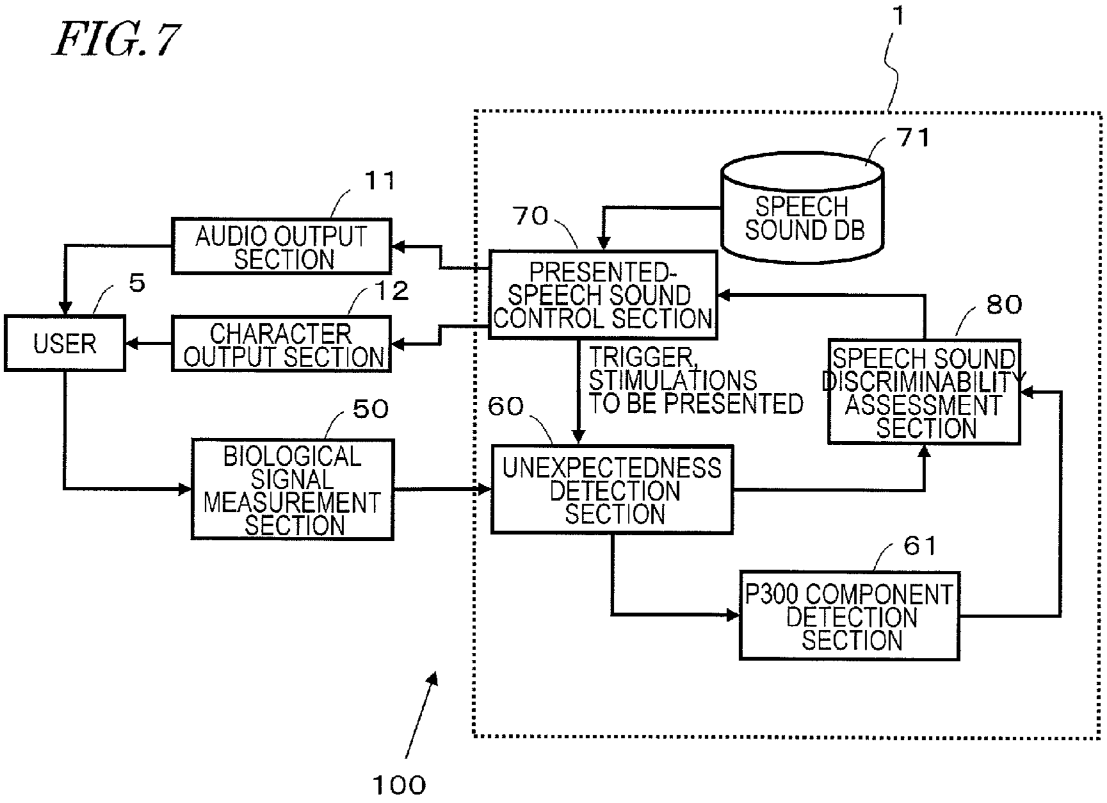
FIG. 7 is a diagram showing a functional block construction of a speech discriminability assessment system 100 according to an embodiment.

FIG. 7 shows a functional block construction of the speech discriminability assessment system 100 according to the present embodiment. The speech discriminability assessment system 100 includes the audio output section 11, the character output section 12, the biological signal measurement section 50, and the speech discriminability assessment apparatus 1. FIG. 7 also shows detailed functional blocks of the speech discriminability assessment apparatus 1. The user 5 block is illustrated for ease of explanation.

The respective functional blocks (except the speech sound DB 71) of the speech discriminability assessment apparatus 1 correspond to functions which are realized by the CPU 30, the memory 31, the audio controller 32, and the graphic controller 33 as a whole upon executing the program which has been described in conjunction with FIG. 6.

The speech sound DB 71 is a database of speech sounds for performing a speech discriminability assessment. FIG. 8 shows an exemplary speech sound DB 71. In the speech sound DB 71 shown in FIG. 8, the audio files and character information to be presented and grouped data based on likelihood of confusion (how likely confusion will occur) are associated. The speech sounds to be stored may be speech sounds that are in the 57S list or the 67S list.

The grouped data is referred to when presenting a character not matching the audio, and is utilized when the user 5 evaluates which groups share a high likelihood of confusion. The grouping may be a rough category, a medium category, and a fine category, for example.

The rough category concerns categorization as to vowels, unvoiced consonants, and voiced consonants, which are respectively represented as 0, 1, and 2. The medium category defines sub-categorization among unvoiced consonants and among voiced consonants. The unvoiced consonants can be categorized into the sa-row (medium category: 1) and the ta-/ka-/ha-rows (medium category: 2), whereas the voiced consonants can be categorized into the ra-/ya-/wa-rows (medium category: 1) and the na-/ma-/ga-/za-/da-/ba-rows (medium category: 2). The fine category can be divided into the na- and ma-rows (fine category: 1) and the za-/ga-/da-/ba-rows (fine category: 2), for example. As for likelihood of confusion, the inventors relied on "HOCHOKI FITTINGU NO KANGAEKATA (or "Concept of Hearing Aid Fitting") (Kazuoki KODERA, Shindan To Chiryosha, 1999).

FIG. 7 is again referred to. The presented-speech sound control section 70 determines a speech sound to be presented by referring to the speech sound DB 71. The speech sound may be selected and determined by random order, or determined by receiving information of speech sounds which are yet to be evaluated or to be evaluated again from the speech discriminability assessment section 100, for example. Moreover, in order to obtain information as to which speech sound will suffer a high likelihood of confusion, the presented-speech sound control section 70 intentionally selects a character not matching the presented audio. Selecting a mismatching character means selecting a character which is not associated with the presented audio in the speech sound DB 71. Any arbitrary character may be selected so long as it is not associated with the audio. For example, by utilizing the grouped information stored in the speech sound DB 71, one may be selected from a row of a close group while conserving the vowel, or a character with a different vowel may be selected while conserving the consonant. Note that selection of a matching character is achieved by selecting a "character" which is associated with the audio file of the presented audio in the speech sound DB 71.

The presented-speech sound control section 70 presents the audio and character thus determined to the user 5 via the audio output section 11 and the character output section 12, respectively. Moreover, it sends a trigger and the actual audio and character to be presented to the unexpectedness detection section 60, in accordance with the point of character presentation.

The audio output section 11 reproduces the monosyllabic audio which is designated by the presented-speech sound control section 70, and presents it to the user 5.

The character output section 12 presents the monosyllabic character which is designated by the presented-speech sound control section 70 to the user 5.

The biological signal measurement section 50, which is an electroencephalograph for measuring a biological signal of the user 5, measures an electroencephalogram as the biological signal. It is assumed that the user 5 has already put on the electroencephalograph.

Based on the trigger received from the presented-speech sound control section 70 as a starting point, the unexpectedness detection section 60 cuts out an event-related potential in a predetermined zone (e.g., a zone from −100 to 1000 ms) from the electroencephalogram of the user 5, which has been measured by the biological signal measurement section 50.

Thereafter, the unexpectedness detection section 60 takes an arithmetic mean of the event-related potential which has been cut out, in accordance with the actual audio and character to be presented received from the presented-speech sound control section 70. The arithmetic mean is to be taken separately depending on whether the speech sound of the audio and the speech sound of the character are matching or mismatching. For example, in the case where they are mismatching, the arithmetic mean is to be taken for each of the rough category, the medium category, and the fine category of the grouping. The rough category, the medium category, and the fine category as mentioned herein refer to the categorizations which have been described with reference to FIG. 8.

By thus calculating an arithmetic mean, a summed waveform is obtained for each of "matching" and the rough category, the medium category, or the fine category of "mismatching", with more than a few summations being made. This makes possible the measurement as to which group a confusion has occurred with. Next, the unexpectedness detection section 60 identifies an event-related potential, and determines the presence or absence of an unexpectedness signal.

The unexpectedness detection section 60 identifies the presence or absence of an unexpectedness signal by the following method. For example, the unexpectedness detection section 60 compares the maximum amplitude from a latency of 550 to 650 ms, or the zone average potential from a latency of 500 to 700 ms, against a predetermined threshold value. Then, if the zone average potential is greater than the threshold value, the case may be identified as "unexpected"; if it is smaller, the case may be identified as "not unexpected". Alternatively, based on a similarity level (e.g., a correlation coefficient) with respect to a predetermined template which is generated from the waveform of a typical unexpectedness signal, the unexpectedness detection section 60 may identify any similar case as "unexpected", and identify any dissimilar case as "not unexpected". The predetermined threshold value or template may be calculated or generated from a prestored waveform of an unexpectedness signal of a generic user, or calculated or generated from the waveform of an unexpectedness signal of each individual person.

If an unexpectedness signal is detected by the unexpectedness detection section 60, the P300 component detection section 61 receives information representing the event-related potential from the unexpectedness signal detection section 60, and determines the presence or absence of a P300 component.

The P300 component detection section 61 identifies the presence or absence of a P300 component by the following method. For example, the P300 component detection section 61 compares the maximum amplitude from a latency of 250 to 350 ms, or the zone average potential from a latency of 250 to 350 ms, against a predetermined threshold value. Then, if the zone average potential is greater than the threshold value, the case may identified as "there is a P300 component"; and if it is smaller, the case may be identified as "no P300 component". Alternatively, based on a similarity level with respect to a predetermined template which is generated from the waveform of a typical P300 component, the P300 component detection section 61 may distinguish any similar case as "there is a P300 component", and any dissimilar case as "no P300 component". The predetermined threshold value or template may be calculated or generated from a prestored waveform of a P300 component of a generic user, or calculated or generated from the waveform of a P300 component of each individual person.

From the unexpectedness detection section 60, the speech discriminability assessment section 80 receives information concerning the presence or absence of an unexpectedness signal with respect to a matching or mismatching character for each speech sound. In the case where there is no unexpectedness signal, the speech discriminability assessment section 80 further receives information concerning the presence or absence of a P300 signal from the P300 component detection section 61. Based on such received information, the speech discriminability assessment section 100 evaluates a speech sound discriminability.

FIG. 9 shows exemplary assessment criteria for discriminability. As shown in FIG. 9, according to the criteria shown in FIG. 9, a speech discriminability assessment is made based on the matching/mismatching between the audio and the character and the presence or absence of an unexpectedness signal and a P300 component, where "○" represents a high discriminability, "X" represents a low discriminability, and "–" represents an uncertain discriminability. In the case of an uncertain discriminability ("–"), the speech discriminability assessment section 80 sends information as to which speech sound was uncertain to the presented-speech sound control section 70, thus instructing the presented-speech sound control section 70 to present the speech sound again. As the speech sound is presented again, eventually all speech sounds will be evaluated into either "○" or "X".

FIG. 10 shows exemplary results of speech discriminability assessment. As shown in FIG. 10, for each speech sound, a ○/X assessment can be made for each of "matching" and the rough category, the medium category, or the fine category of "mismatching". As a result, in the case of a low speech sound discriminability, e.g., a speech sound "な" in FIG. 10, the group(s) with which its aural distinction is difficult becomes clear. Moreover, potentially-low clarities can also be detected, e.g., "や", which permits matching between the audio and the character to be correctly identified but may induce a mistake in listening comprehension with respect to the medium category. Moreover, a probability of "○" (which represents an "high speech sound discriminability" assessment) may be calculated with respect to each speech sound, and the calculated probability of high discrimination score may be defined as the final speech discriminability assessment.

3.2. Operation of Speech Discriminability Assessment System

Figure 11:
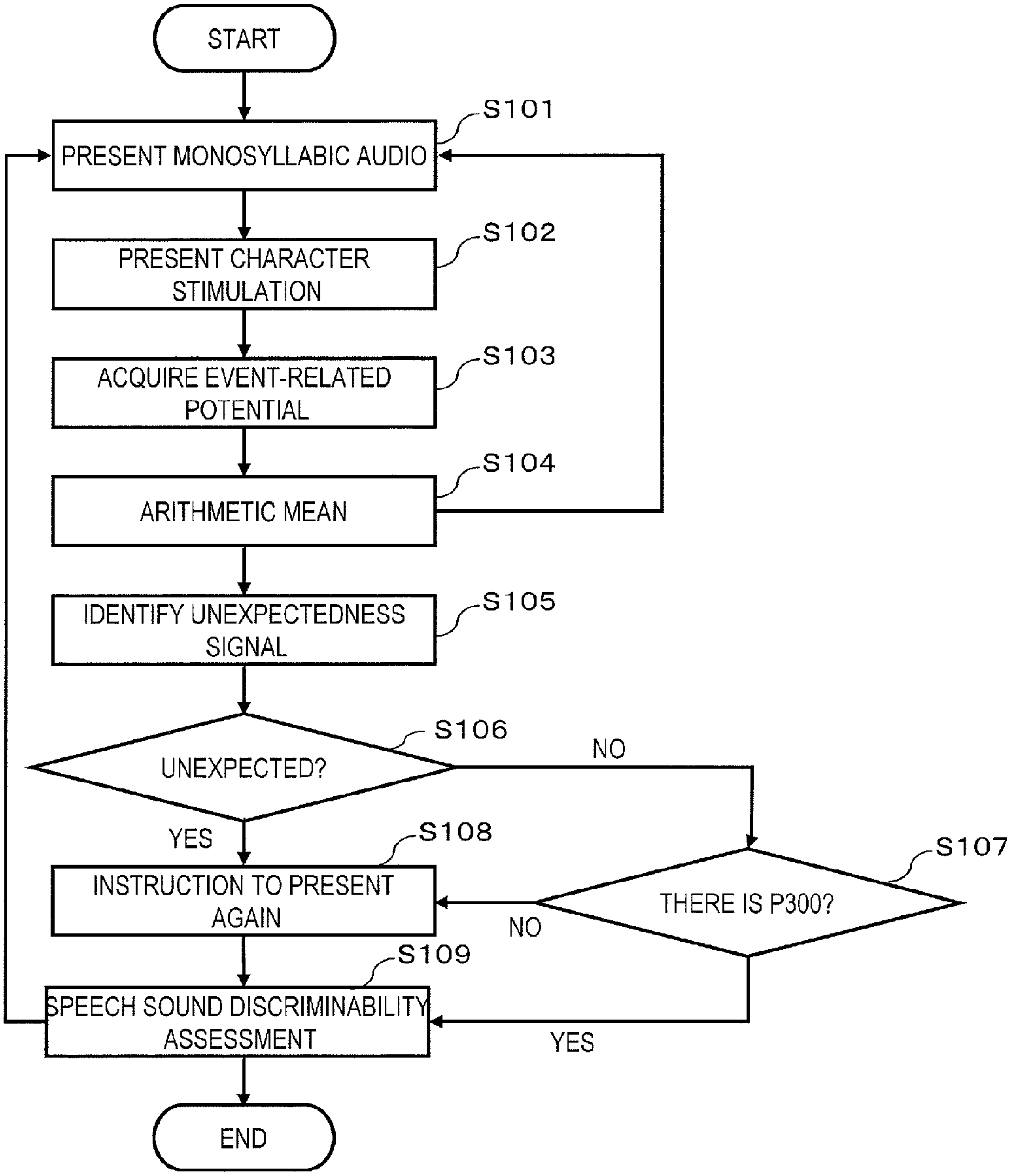
FIG. 11 is a flowchart showing a procedure of processing performed by the speech discriminability assessment system 100.

Next, with reference to FIG. 11, an overall processing procedure performed by the speech discriminability assessment system 100 of FIG. 7 will be described. FIG. 11 is a flowchart showing a procedure of processing performed by the speech discriminability assessment system 100.

At step S101, by referring to the speech sound DB 71, the presented-speech sound control section 70 determines a monosyllabic speech sound to be presented, presents the audio to the user 5 via the audio output section 11, and sends the information of the presented audio to the unexpectedness detection section 60. The speech sound to be presented may be randomly selected from the DB 71, or determined by receiving information of speech sounds which are yet to be evaluated or to be evaluated again from the speech discriminability assessment section 100.

At step S102, by referring to the speech sound DB 71, the presented-speech sound control section 70 selects and determines a character to be presented, and presents the character to the user 5 via the character output section 12. Moreover, the presented-speech sound control section 70 sends a trigger and the information of the selected character to the unexpectedness detection section 60 at the time of presenting the character. As for the character selection, a character matching the audio that has been presented at step S101 may be selected, or a character not matching the audio may be intentionally selected by referring to the grouping which is stored in the speech sound DB 71.

At step S103, upon receiving the trigger from the presented-speech sound control section 70, the unexpectedness detection section 60 cuts out an event-related potential, e.g. from −100 to 1000 ms based on the trigger as a starting point, from the electroencephalogram measured by the biological signal measurement section 50. Then, a baseline correction to the average potential from −100 to 0 ms is performed.

At step S104, based on the information of the speech sound to be presented which is received from the presented-speech sound control section 70, the unexpectedness detection section 60 takes an arithmetic mean of the event-related potential cut out at step S103. As used herein, "information of the speech sound to be presented" contains information as to whether the presented speech sound (presented audio) and the character are matching or mismatching. Moreover, the arithmetic mean is taken separately depending on whether the speech sound of the audio and the speech sound of the character are matching or mismatching. For example, in the case where they are mismatching, the arithmetic mean is to be taken for each of the rough category, the medium category, and the fine category of the grouping.

At step S105, the unexpectedness detection section 60 identifies the waveform of the event-related potential whose arithmetic mean has been taken at step S104, and determines the presence or absence of an unexpectedness signal. As described above, the identification of an unexpectedness signal may be made based on a comparison against a threshold value, or based on a comparison against a template.

At step S106, a branching occurs as to whether an unexpectedness signal has been detected or not in the unexpectedness signal identification of step S105. If an unexpectedness signal has been detected by the unexpectedness detection section 60, the process proceeds to step S108; if not, the process proceeds to step S107.

At step S107, the P300 component detection section 61 receives information representing an event-related potential from the unexpectedness detection section 60, and identifies whether a P300 component exists or not. If a P300 component is identified, the process proceeds to step S109; if not, the process proceeds to step S108. As described above, based on a comparison against a threshold value, or based on a comparison against a template.

At step S108, the speech discriminability assessment section 80 sends information identifying a speech sound whose discriminability was uncertain to the presented-speech sound control section 70, thus instructing the presented-speech sound control section 70 to present the speech sound again.

At step S109, from the unexpectedness detection section 60, the speech discriminability assessment section 100 receives information concerning the presence or absence of an unexpectedness signal with respect to a matching/mismatching character for each speech sound, and if there is an unexpectedness signal, further receives information concerning the presence or absence of a P300 signal from the P300 component detection 61 and makes a speech discriminability assessment.

Note that the procedure of returning to step S101 from step S109 means repeating the process for another trial. A speech discriminability assessment including the result of step S108 is performed, and a speech sound to be next presented is determined.

As for the criteria of speech discriminability assessment, as shown in FIG. 9, the assessment is made based on the matching/mismatching between the audio and the character and the presence or absence of an unexpectedness signal and a P300 component, where "○" represents a high discriminability, "X" represents a low discriminability, and "−" represents an uncertain discriminability. In the case of an uncertain discriminability, information as to which speech sound was uncertain is sent to the presented-speech sound control section 70, thus instructing the presented-speech sound control section 70 to present the speech sound again.

Through the above process, on the premise that a monosyllabic speech sound(s) is sequentially presented in the form of an audio and a character, under a condition such that characters which do not match the audio are presented with a predetermined probability, a detailed speech discriminability assessment can be conducted by using an unexpectedness signal and a P300 component within an event-related potential based on the point of character presentation as a starting point.

The above-described Embodiment illustrates an exemplary application to a Japanese environment. However, any other language, e.g., English or Chinese, may be used so long as the speech sounds are momentary. In the case of English, for example, monosyllabic words such as those shown in FIG. 17A may be presented in the form of audios and characters, and an assessment may be made on a word-by-word basis. Alternatively, an assessment may be made on a phonetic symbol-by-phonetic symbol basis, as shown in FIG. 17B.

Moreover, the presented-speech sound control section 70 may make the selection between a character matching the audio presented at step S101 and a mismatching character by relying on a change in the amplitude of an event-related potential in a zone of 600 ms±100 ms based on the point in time of presenting the character as a starting point.

With respect to either matching/mismatching between the audio and the character, the unexpectedness detection section 60 stores information of the amplitude of an event-related potential in the aforementioned zone in chronological order. Then, with respect to either matching/mismatching between the audio and the character, the unexpectedness detection section 60 determines a change in amplitude of that event-related potential. Note that the information concerning the amplitude of an event-related potential and a change in amplitude of an event-related potential is recorded and stored in a recording section which is provided in the interior of the unexpectedness detection section 60, for example. As such a recording section, a memory 31 (FIG. 6) in which the computer program 35 and the speech sound DB 71 are stored may be utilized, or a storage medium (e.g., a flash memory or a hard disk) different from the memory 31 may be used.

If a change in the amplitude of the event-related potential when the audio and the character are matching is smaller than (or equal to) a change in the amplitude of the event-related potential when the audio and the character are mismatching, the presented-speech sound control section 70 increases the frequency of selecting the character which matches the presented audio. On the other hand, if a change in the amplitude of the event-related potential when the audio and the character are matching is greater than a change in the amplitude of the event-related potential when the audio and the character are mismatching, the presented-speech sound control section 70 increases the frequency of selecting a character that does not match the presented audio.

As a result, concerning the matching or mismatching case between the audio and the character, an event-related potential associated with whichever has a smaller change in amplitude can be amply measured. Therefore, since there is more waveform information for taking a sum of the event-related potential in the case of a small change in amplitude, the accuracy of determining the presence or absence of an unexpectedness signal can be improved.

According to the speech discriminability assessment system 100 of the present embodiment, a speech discriminability assessment is realized as the user merely hears an audio and confirms a character, without answer inputs being made. As a result, the trouble which the user incurs for making an assessment is significantly reduced.

4. Embodiment 2

The speech discriminability assessment system 100 according to Embodiment 1 evaluates a speech sound discriminability with respect to an audio which is stored in the speech sound DB 71, by sequentially presenting the audio and a character and examining the presence or absence of an unexpectedness signal in response to the presentation of the character. However, since only the presence or absence of an unexpectedness is determined, and the speech discriminability assessment is performed on a ○/X basis, the resolution thereof may not be so high that fine differences in fitting parameters will be reflected on the result of discriminability assessment. As mentioned earlier, currently there is no one established fitting method for hearing aids, and several approaches are diversely present, and thus an optimum fitting method must be found for each user. Therefore, in the present embodiment, a speech discriminability assessment system will be described which makes an assessment as to which fitting parameter is appropriate among a plurality of fitting parameters.

Fitting is realized by making a gain adjustment for each frequency, based on the relationship between the shape of an audiogram, a threshold value which is determined through a subjective report, a UCL, and an MCL (Most comfortable level: a sound loudness that is aurally comfortable to a user). According to page 79 of "HOCHOKI Q&A—YORIYOI FITTINGU NOTAMENI" (or "Hearing aids Q&A—For better fitting") (Zin KANZAKI et al., KANEHARA & Co., LTD., 2001), there are following types of fitting methods, for example: the half-gain method, in which an insertion gain of each frequency is made half of the hearing threshold level of that frequency; Berger's method, which, in addition to the above, slightly augments the gains from 1000 Hz to 4000 Hz by taking into consideration the frequency band and level of conversational voices; and the POGO method, which, based on the half-gain method, reduces the gains at 250 Hz and 500 Hz (where there is not so much speech sound information but a lot of noise component is included) by 10 dB and 5 dB, respectively; and the NAL-R method, which performs amplification so that a frequency of long-term sound analysis of words will fall around a comfortable level.

Therefore, a speech discriminability assessment system according to the present embodiment converts audio data stored in the speech sound DB 71 by using several fitting methods, as is done by an actual hearing aid, presents a plurality of kinds of converted audios to a user, and makes an assessment as to which fitting method is the best by utilizing the amplitude of an unexpectedness signal. This takes advantage of a tendency which became clear through the aforementioned experimental results that the amplitude of an unexpectedness signal reflects a degree of mismatching between the audio and the character that is felt by the user. Conversion into the plurality of kinds of audios is realized by adjusting the sound level for each frequency. For example, in the case where the half-gain method is used as the fitting method, the gain of each frequency is adjusted to be a half of the hearing threshold level, based on an audiogram of the user.

Figure 12:
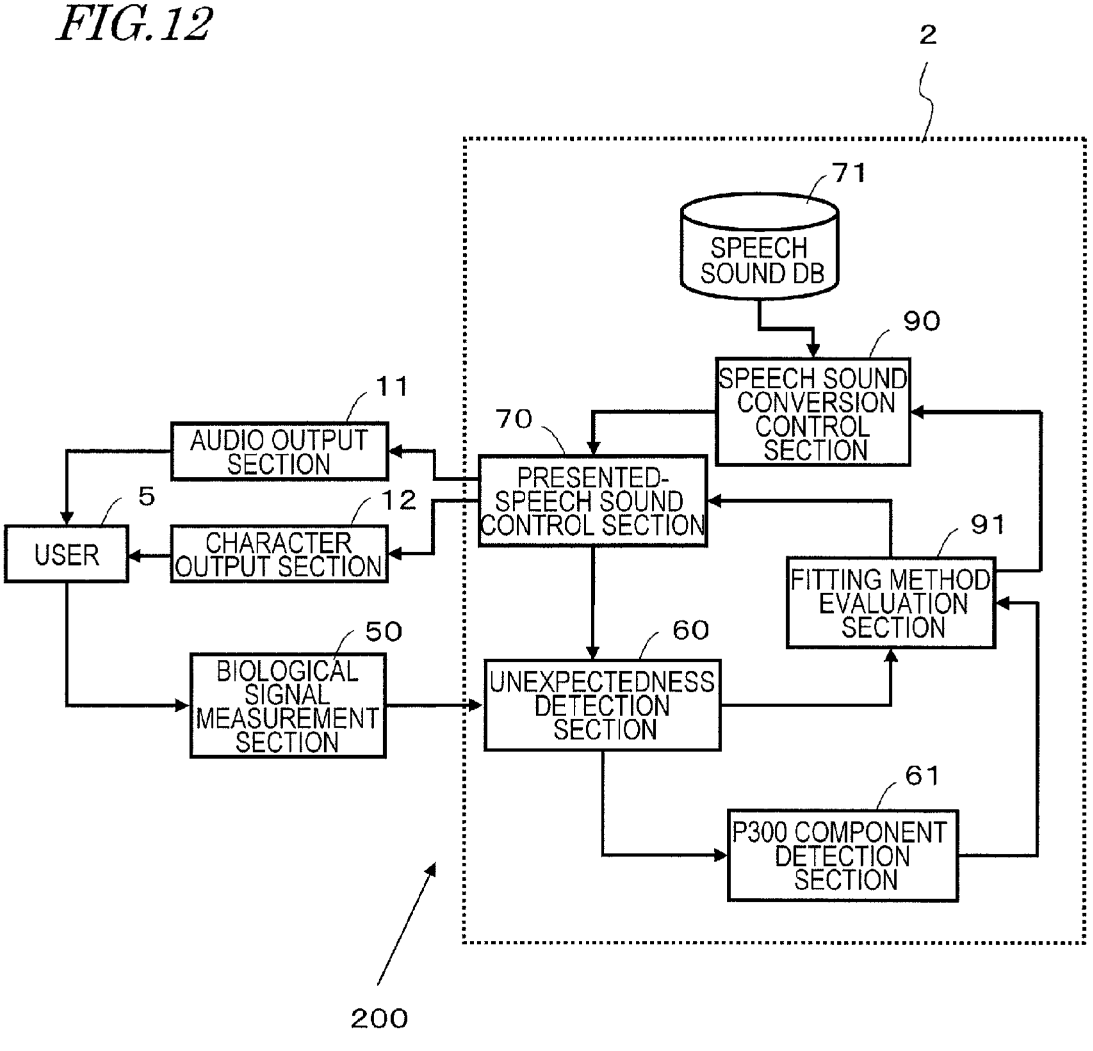
FIG. 12 is a diagram showing a functional block construction of a speech discriminability assessment system 200 according to Embodiment 2.

FIG. 12 shows a functional block construction of a speech discriminability assessment system 200 according to the present embodiment. The speech discriminability assessment system 200 includes the audio output section 11, the character output section 12, the biological signal measurement section 50, and a speech discriminability assessment apparatus 2. Any block which has an identical counterpart in FIG. 7 is denoted by a like reference numeral, and the description thereof is omitted. The hardware construction of the speech discriminability assessment apparatus 2 is as shown in FIG. 6. The speech discriminability assessment apparatus 2 of the present embodiment shown in FIG. 12 is realized as a program which defines a different process from that of the program 35 (FIG. 6) is executed.

In the present embodiment, it is assumed that the user is wearing a hearing aid in advance because an assessment of a plurality of fitting methods is to be made. Instead of wearing a hearing aid, however, an audio which has been subjected to each fitting method may be output through the audio output section 11 (loudspeakers) shown in FIG. 5, for example.

The speech discriminability assessment apparatus 2 of the present embodiment differs from the speech discriminability assessment apparatus 1 of Embodiment 1 in that, instead of the speech discriminability assessment section 80, a speech sound conversion control section 90 and a fitting method evaluation section 91 are provided.

Hereinafter, the speech sound conversion control section 90 and the fitting method evaluation section 91 will be described.

Based on an audiogram of the user 5 which was previously measured, the speech sound conversion control section 90 converts each audio data that is stored in the speech sound DB 71 in light of a plurality of types of fitting methods. As mentioned above, possible fitting methods include the half-gain method, the Berger method, the POGO method, the NAL-R method, and the like.

From the unexpectedness detection section 60, as the amplitude of an event-related potential based on the point of character presentation as a starting point, the fitting method evaluation section 91 receives information of a zone average potential from a latency of 500 to 700 ms, for example. Furthermore, in the absence of an unexpectedness signal, the fitting method evaluation section 91 receives information concerning the presence or absence of a P300 signal from the P300 component detection section 61. Note that the information to be acquired from the unexpectedness detection section 60 may be the maximum amplitude from a latency of 550 to 650 ms.

Then, regarding each fitting method, the fitting method evaluation section 91 takes an arithmetic mean of the amplitude of an event-related potential with respect to the mismatching and matching cases between the audio stimulation and the character stimulation, for all speech sounds used in the test, and calculates the amplitude of an unexpectedness signal (LPP) by subtracting the amplitude of the matching cases from the amplitude of the mismatching cases.

FIG. 13 shows amplitudes of various event-related potentials respectively calculated for fitting methods A to C. For example, fitting method A is the half-gain method, fitting method B is the Berger method, and fitting method C is the POGO method.

Next, the fitting method evaluation section 91 compares the amplitudes of the unexpectedness signals (LPP) obtained by the respective fitting methods. When there is a high speech sound discriminability, the unexpectedness signal in response to a stimulation of a character that does not match the audio has a large amplitude, and no amplitude appears in response to a stimulation of a character that matches the audio. Therefore, the final unexpectedness signal (LPP), which is obtained through a subtraction between them, has a large amplitude. On the other hand, when the speech sound discriminability is low, the unexpectedness signal in response to a stimulation of a character that does not match the audio has a small amplitude, and some unexpectedness signal also appears in response to a stimulation of a character that matches the audio due to incorrect listening comprehension; therefore, the final unexpectedness signal (LPP) has a small amplitude. Thus, based on the LPP amplitude, it is possible to rank the fitting methods in terms of which one is the best for the user 5.

FIG. 14 shows exemplary assessment results of fitting methods. These assessment results are calculated based on the example of FIG. 13. FIG. 14 illustrates an example where, based on the LPP amplitude, fitting method A having a large LPP amplitude is evaluated as "⊚" (meaning the fitting method is suitable to the user 5) and fitting method B having a small LPP amplitude is evaluated as "X" (not suitable).

Although the LPP amplitude calculation may be performed with respect to only one sound, a higher accuracy can be obtained by performing LPP amplitude calculations with respect to a large number of sounds and performing the aforementioned process based on an average of differences.

In the aforementioned process (FIG. 14), each fitting method is granted either a "⊚", "X" or "Δ" assessment depending on the LPP amplitude level; however, this is only an example. So long as an optimum fitting method can be selected, the method of indication can be arbitrary. Moreover, a threshold value against which each LPP amplitude level is to be compared may be determined in advance, and any fitting method may be indicated to the user as appropriate if that threshold value is exceeded.

Next, with reference to a flowchart of FIG. 15, an overall procedure of processing performed by the speech discriminability assessment system 200 will be described.

Figure 15:
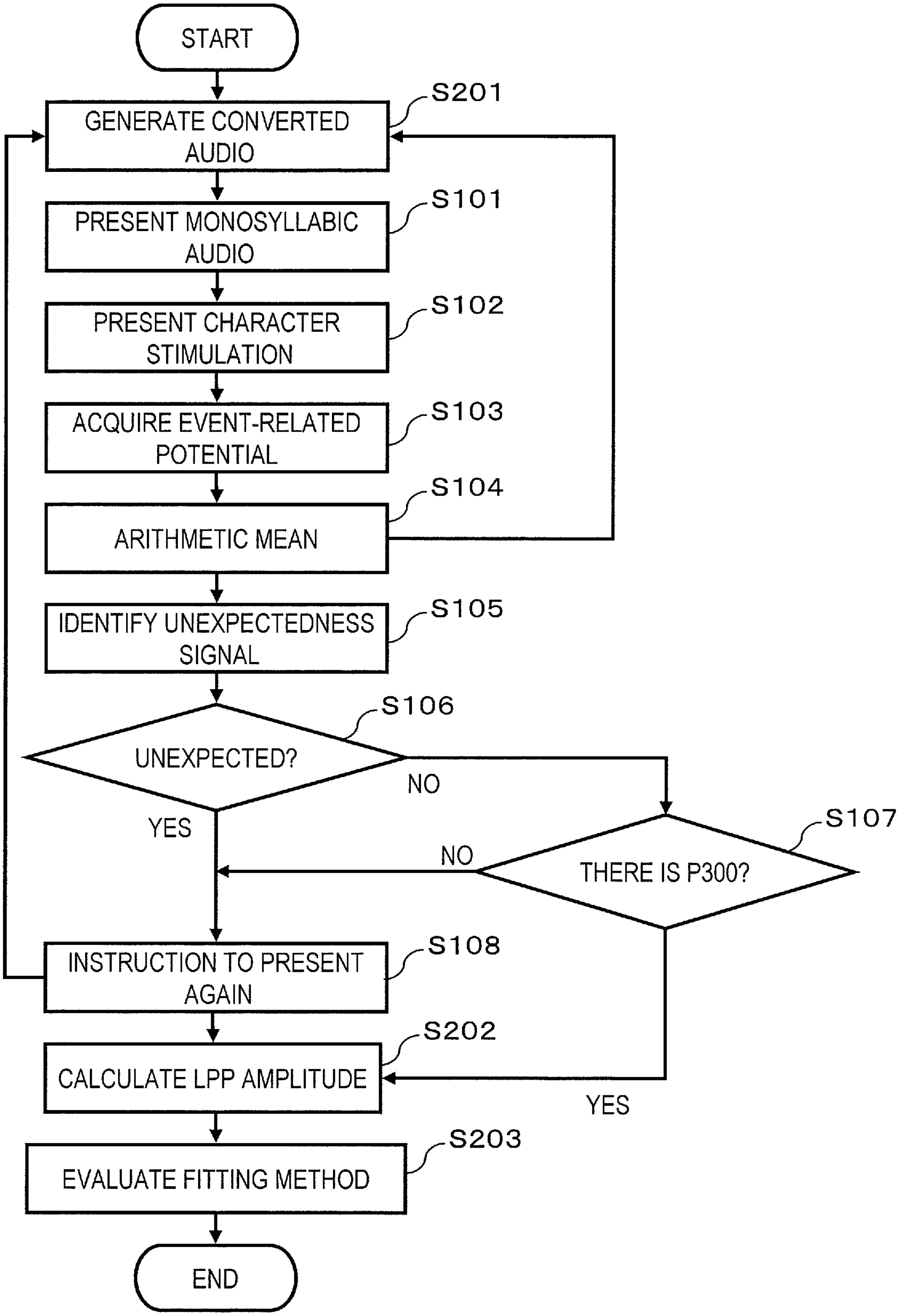
FIG. 15 is a flowchart showing a processing procedure by the speech discriminability assessment system 200 according to Embodiment 2.

FIG. 15 shows a processing procedure by the speech discriminability assessment system 200 according to the present embodiment. In FIG. 15, any step where an identical process to a process of the speech discriminability assessment system 100 (FIG. 11) is performed is denoted by a like reference numeral, and the description thereof is omitted.

The processes by the speech discriminability assessment system 200 of the present embodiment differs from the processes of the speech discriminability assessment system 200 of Embodiment 1 in that step S201, step S202, and step S203 are newly introduced.

At step S201, by referring to the speech sound DB and an audiogram of the user 5 which was previously measured, the speech sound conversion control section 90 generates a plurality of sets of audios for each fitting method.

At step S202, the fitting method evaluation section 91 takes an arithmetic mean of the information of the amplitude of an event-related potential received from the unexpectedness detection section 60 with respect to the mismatching and matching cases between the audio stimulation and the character stimulation in each fitting method, for all speech sounds used in the test, and calculates an LPP amplitude by subtracting the amplitude of the matching cases from the amplitude of the mismatching cases.

At step S203, based on the LPP amplitudes calculated at step S203, the fitting method evaluation section 91 indicates the fitting method that has the greatest LPP amplitude to the user as an optimum fitting method.

Through such processes, the amplitude of an unexpectedness signal is calculated for each type of fitting method, and for each speech sound of each fitting method, thus making it possible to find a fitting method that is optimum to the user through amplitude comparison. Thus, evaluations of fitting methods can be made.

In accordance with the speech discriminability assessment system 200 of the present embodiment, it is possible to automatically ascertain an optimum fitting method for each user. This eliminates the need for any fitting to made for searching purposes, and thus significantly reduces the amount of time required for fitting.

Although the present embodiment illustrates a case of calculating an LPP amplitude by subtracting the amplitude of an event-related potential of matching cases from the event-related potential amplitude of mismatching cases, this is only an example. Instead of determining an LPP amplitude through subtraction, a rate (ratio) of an event-related potential amplitude of the mismatching cases to an event-related potential amplitude of the matching cases may be calculated. Then, the fitting method evaluation section 91 may indicate the fitting method that has the greatest ratio to the user as an optimum fitting method.

In accordance with a speech discriminability assessment apparatus of the present invention and a speech discriminability assessment system in which the speech discriminability assessment apparatus is incorporated, a speech discriminability assessment can be realized without answer inputs being made by a user. Moreover, it is possible to identify a fitting method that is optimum for the user. Thus, fitting of a hearing aid can be performed with ease and high accuracy, as a result of which users of hearing aids are expected to increase drastically.

While the present invention has been described with respect to preferred embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. A speech discriminability assessment system, comprising:

a biological signal measurement processor configured to measure an electroencephalogram signal of a user;

a presented-speech sound control processor configured to determine a speech sound to be presented to the user by referring to a speech sound database retaining a plurality of monosyllabic sound data;

an audio presentation processor configured to present an audio associated with the determined speech sound to the user;

a character presentation processor configured to present a character associated with the determined speech sound to the user, subsequent to the presentation of the audio by the audio presentation processor;

an unexpectedness detection processor configured to detect presence or absence of an unexpectedness signal from the measured electroencephalogram signal of the user, the unexpectedness signal representing a positive component at 600 ms±100 ms after a time point when the character was presented to the user; and a speech sound discriminability determination processor configured to determine a speech sound discriminability based on a result of detection by the unexpectedness detection processor.

2. The speech discriminability assessment system of claim 1, wherein the presented-speech sound control processor presents a character that does not match the audio with a predetermined frequency of occurrence.

3. The speech discriminability assessment system of claim 2, wherein, the speech sound discriminability determination processor is configured to:

when the character presented to the user matches the audio presented to the user, make a low discriminability determination if a positive component exists at 600 ms±100 ms based on a point of presenting the character as a starting point;

make a high discriminability determination if no positive component exists at 600 ms±100 ms based on a point of presenting the character as a starting point and a positive component exists at 300 ms±100 ms based on a point of presenting the character as a starting point; and determine a failure of the user to look at the character presented at the character presentation processor if no positive component exists at 600 ms±100 ms based on a point of presenting the character as a starting point and no positive component exists at 300 ms±100 ms based on a point of presenting the character as a starting point; and when the character presented to the user does not match the audio presented to the user, make a high discriminability determination if a positive component exists at 600 ms±100 ms based on a point of presenting the character as a starting point;

make a low discriminability determination if no positive component exists at 600 ms±100 ms based on a point of presenting the character as a starting point and a positive component exists at 300 ms±100 ms based on a point of presenting the character as a starting point; and determine a failure of the user to look at the character presented at the character presentation processor if no positive component exists at 600 ms±100 ms based on a point of presenting the character as a starting point and no positive component exists at 300 ms±100 ms based on a point of presenting the character as a starting point.

4. The speech discriminability assessment system of claim 2, wherein, with respect to either matching or mismatching between the audio and the character, the unexpectedness detection processor stores information of amplitude of an event-related potential at 600 ms±100 ms based on a point of presenting the character as a starting point, and determines a change in the amplitude of the event-related potential with respect to either matching or mismatching between the audio and the character; and the presented-speech sound control processor is configured to:

if the change in amplitude of the event-related potential when the audio and the character are matching is equal to or less than the change in amplitude of the event-related potential when the audio and the character are mismatching, increase a frequency of selecting a character that matches the presented audio; and if the change in amplitude of the event-related potential when the audio and the character are matching is greater than the change in amplitude of the event-related potential when the audio and the character are mismatching, increase a frequency of selecting a character that does not match the presented audio.

5. The speech discriminability assessment system of claim 1, wherein, the speech sound discriminability determination processor is configured to:

when the character presented to the user matches the audio presented to the user, make a low discriminability determination if a positive component exists at 600 ms±100 ms based on a point of presenting the character as a starting point, and make a high discriminability determination if no positive component exists at 600 ms±100 ms based on a point of presenting the character as a starting point; and when the character presented to the user does not match the audio presented to the user, make a high discriminability determination if a positive component exists at 600 ms±100 ms based on a point of presenting the character as a starting point, and make a low discriminability determination if no positive component exists at 600 ms±100 ms based on a point of presenting the character as a starting point.

6. The speech discriminability assessment system of claim 1, further comprising a P300 component detection processor configured to determine, from the electroencephalogram signal of the user as measured by the biological signal measurement section, presence or absence of a positive component at 300 ms±50 ms based on a point of presenting the character as a starting point, wherein, if the unexpectedness detection processor determines that no positive component exists, the P300 component detection processor determines presence or absence of a positive component at 300 ms±50 ms, and the speech sound discriminability determination processor determines the speech sound discriminability based on a result of detection by the unexpectedness detection processor and on a result of detection by the P300 component detection processor.

7. The speech discriminability assessment system of claim 1, wherein, in the speech sound database, an audio, a character, and a group concerning likelihood of confusion are associated with a common speech sound.

8. The speech discriminability assessment system of claim 7, wherein, in the speech sound database, an audio, a character, and a group concerning likelihood of confusion are associated with each of a plurality of speech sounds.

9. The speech discriminability assessment system of claim 8, wherein, referring to the groups concerning likelihood of confusion in the speech sound database, the presented-speech sound control processor presents a character not associated with the audio with a predetermined frequency of occurrence.

10. The speech discriminability assessment system of claim 9, wherein the speech sound discriminability determination processor evaluates a speech sound discriminability with respect to each group concerning likelihood of confusion when the audio and the character are of different speech sounds, in addition to when the character presented to the user matches the audio presented to the user.

11. The speech discriminability assessment system of claim 1, further comprising a speech sound conversion control processor configured to convert an audio stored in the speech sound database into a plurality of kinds of audios in accordance with different fitting methods for a hearing aid worn by the user.

12. The speech discriminability assessment system of claim 11, wherein, when the plurality of kinds of audios converted by the speech sound conversion control processor are presented via the audio presentation processor, the speech sound discriminability determination processor makes a comparison between amplitudes of event-related potentials obtained for the different fitting methods, and determines a fitting method that is suitable to the user in accordance with a result of comparison.

13. A speech discriminability assessment method, comprising the steps of:

determining a speech sound to be presented by referring to a speech sound database retaining a plurality of monosyllabic sound data, and presenting the audio;

determining a speech sound to be presented by referring to the speech sound database, and presenting a character subsequent to the presentation of the audio;

measuring an electroencephalogram signal of a user;

from the measured electroencephalogram signal of the user, determining presence or absence of a positive component at 600 ms±100 ms based on a point of presenting the character as a starting point; and determining a speech sound discriminability based on a result of detection by an unexpectedness detection processor.

14. The speech discriminability assessment method of claim 13, wherein, with a predetermined frequency of occurrence, the step of presenting the character presents a character that does not match the audio.

15. The speech discriminability assessment method of claim 14, wherein, the step of determining presence or absence of a positive component stores information of amplitude of an event-related potential at 600 ms±100 ms based on a point of presenting the character as a starting point, with respect to either matching or mismatching between the audio and the character, and determines a change in the amplitude of the event-related potential with respect to either matching or mismatching between the audio and the character; and the step of presenting the character comprises:

if a change in amplitude of the event-related potential when the audio and the character are matching is equal to or less than a change in amplitude of the event-related potential when the audio and the character are mismatching, presenting the character with an increased frequency of selecting a character that matches the presented audio, and if a change in amplitude of the event-related potential when the audio and the character are matching is greater than a change in amplitude of the event-related potential when the audio and the character are mismatching, presenting the character with an increased frequency of selecting a character that does not match the presented audio.

16. A non-transitory computer-readable medium storing a computer program to be executed by a computer, wherein the computer program causes the computer to execute the steps of:

determining a speech sound to be presented by referring to a speech sound database retaining a plurality of monosyllabic sound data, and presenting audio;

determining a speech sound to be presented by referring to the speech sound database, and presenting a character subsequent to the presentation of the audio;

measuring an electroencephalogram signal of a user;

from the measured electroencephalogram signal of the user, determining presence or absence of a positive component at 600 ms±100 ms based on a point of presenting the character as a starting point; and determining a speech sound discriminability based on a result of detection by an unexpectedness detection processor.

17. The non-transitory computer-readable medium of claim 16, wherein the step of presenting the character presents a character that does not match the audio with a predetermined frequency of occurrence.

18. A speech discriminability assessment system, comprising:

a presented-speech sound control processor configured to determine a speech sound to be presented to a user by referring to a speech sound database retaining a plurality of monosyllabic sound data, and performing control so that an audio associated with the determined speech sound is presented to the user via an audio presentation processor configured to present an audio and subsequently a character associated with the determined speech sound is presented to the user via a character presentation processor configured to present a character;

an unexpectedness detection processor configured to detect presence or absence of an unexpectedness signal from an electroencephalogram signal of the user measured by a biological signal measurement processor configured to measure an electroencephalogram signal of the user, the unexpectedness signal representing a positive component at 600 ms±100 ms based on a point of presenting the character to the user as a starting point; and a speech sound discriminability determination processor configured to determine a speech sound discriminability based on a result of detection by the unexpectedness detection processor.

* * * * *